(12) United States Patent
Zhang et al.

(10) Patent No.: US 9,193,967 B2
(45) Date of Patent: *Nov. 24, 2015

(54) PEGYLATED ANALOGUE PROTEIN OR CANINE URATE OXIDASE, PREPARATION METHOD AND USE THEREOF

(76) Inventors: Chun Zhang, Chongqing (CN); Kai Fan, Chongqing (CN); Xuefeng Ma, Chongqing (CN); Li Yang, Chongqing (CN); Chunlan Hu, Chongqing (CN); Hua Luo, Chongqing (CN); Xiang Mei, Chongqing (CN)

( * ) Notice: Subject to any disclaimer, the term of this patent is extended or adjusted under 35 U.S.C. 154(b) by 0 days.

This patent is subject to a terminal disclaimer.

(21) Appl. No.: 13/985,273

(22) PCT Filed: Feb. 14, 2012

(86) PCT No.: PCT/CN2012/071106
§ 371 (c)(1),
(2), (4) Date: Oct. 23, 2013

(87) PCT Pub. No.: WO2012/109975
PCT Pub. Date: Aug. 23, 2012

(65) Prior Publication Data
US 2014/0065123 A1  Mar. 6, 2014

(30) Foreign Application Priority Data

Feb. 14, 2011  (CN) .......................... 2011 1 0037301

(51) Int. Cl.
| A61K 48/00 | (2006.01) |
| C12N 9/96 | (2006.01) |
| A61K 47/48 | (2006.01) |
| C12N 9/06 | (2006.01) |
| A61K 38/00 | (2006.01) |

(52) U.S. Cl.
CPC ............ *C12N 9/96* (2013.01); *A61K 47/48215* (2013.01); *C12N 9/0048* (2013.01); *C12Y 107/03003* (2013.01); *A61K 38/00* (2013.01)

(58) Field of Classification Search
CPC combination set(s) only.
See application file for complete search history.

(56) References Cited

U.S. PATENT DOCUMENTS

| 6,576,235 B1 | 6/2003 | Williams et al. |
| 6,913,915 B2 | 7/2005 | Ensor et al. |
| 7,056,713 B1 | 6/2006 | Hershfield et al. |
| 2012/0269795 A1 | 10/2012 | Fan et al. |
| 2013/0084273 A1 | 4/2013 | Hartman et al. |
| 2013/0330803 A1 | 12/2013 | Hartman et al. |

FOREIGN PATENT DOCUMENTS

| CN | 1322141 | 11/2001 |
| CN | 1322243 | 11/2001 |
| CN | 101194016 | 6/2008 |
| CN | 101198693 | 6/2008 |
| CN | 102051348 | 5/2011 |
| CN | 102260653 | 11/2011 |
| WO | WO-00/07629 | 2/2000 |
| WO | WO-00/08196 | 2/2000 |
| WO | WO-2011/050599 | 5/2011 |

OTHER PUBLICATIONS

Abuchowski et al., "Reduction of plasma urate levels in the cockerel with polyethylene glycol-uricase," J Pharmacol Exp Ther (1981) 219(2):352-354.

Bomalaski et al., "Phase I study of uricase formulated with polyethylene glycol (Uricase-PEG 20)," Arthritis Rheum (2002) 46(9 Suppl.):S141.

Bomalaski et al., "Uricase formulated with polyethylene glycol (uricase-PEG 20): biochemical rationale and preclinical studies," J Rheumatol (2002) 29(9):1942-1949.

Bosly et al., "Rasburicase (recombinant urate oxidase) for the management of hyperuricemia in patients with cancer: report of an international compassionate use study," Cancer (2003) 98(5):1048-1054.

Chen et al., "Properties of two urate oxidases modified by the covalent attachment of poly(ethylene glycol)," Biocheim Biophys Acta (1981) 660:293-298.

Colloc'h et al., Sequence and structural features of the T-fold, an original tunnelling building unit, Proteins (2000) 39:142-154.

Ganson et al., "Control of hyperuricemia in subjects with refractory gout, and induction of antibody against poly(ethylene glycol) (PEG), in a phase I trial of subcutaneous PEGylated urate oxidase," Arthritis Res Therapy (2006) 8:R12.

Hershfield, Gout and uric acid metabolism in: Bennett JC, Plum F (eds.), Cecil's Textbook of Medicine, 20th ed., (1996) pp. 1508-1515, W.B. Saunders Co., Philadelphia.

International Preliminary Report on Patentability and Written Opinion for PCT/CN2012/071106, issued Aug. 21, 2013, 8 pages (English language translation).

International Search Report for PCT/CN2012/071106, issued May 17, 2012, 12 pages (English language translation attached).

Lee et al., "Generation of cDNA probes directed by amino acid sequence: cloning of urate oxidase," Science (1988) 239:1288-1291.

Miao et al., "Dietary and lifestyle changes associated with high prevalence of hyperuricemia and gout in the Shandong coastal cities of Eastern China," J Rheumatol (2008) 35(9):1859-1864.

(Continued)

*Primary Examiner* — Kagnew H Gebreyesus
(74) *Attorney, Agent, or Firm* — Workman Nydegger

(57) ABSTRACT

Provided are a PEGylated analogue protein of canine urate oxidase, preparation method and use thereof. The analogue protein of canine urate oxidase is a canine urate oxidase, or a chimeric protein comprising part of the amino acid sequence of a canine urate oxidase and part of the amino acid sequence of a human urate oxidase, or a mutant protein thereof. The PEGylated analogue protein of canine urate oxidase and pharmaceutical compositions thereof according to the present invention can be used for the prevention and/or treatment of hyperuricemia and chronic gout.

13 Claims, 6 Drawing Sheets

(56) References Cited

OTHER PUBLICATIONS

Navolanic et al., "Elitek-rasburicase: an effective means to prevent and treat hyperuricemia associated with tumor lysis syndrome, a Meeting Report, Dallas, Texas, Jan. 2002," Leukemia (2003) 17(3):499-514.

Nishimura et al., "Modification of yeast uricase with polyethylene glycol: disappearance of binding ability towards anti-uricase serum," Enzyme (1979) 24:261-264.

Retailleau et al., "Urate oxidase from *Aspergillus flavus*: new crystal-packing contacts in relation to the content of the active site," Acta Crystallogr D Biol Crysytallogr (2005) 61:218-229.

Roberts et al., "Chemistry for peptide and protein PEGylation," Adv Drug Deliv Rev (2002) 54:459-476.

Rosenberg, "Effects of protein aggregates: an immunologic perspective," AAPS J (2006) 8(3):E501-507.

Sherman et al., "PEG-uricase in the management of treatment-resistant gout and hyperuricemia," Adv Drug Deliv Rev (2008) 60:59-68.

Tsuji et al., "Studies on antigenicity of the polyethylene glycol (PEG)-modified uricase," Int J Immunopharmacol (1985) 7(5):725-730.

Veronese, "Peptide and protein PEGylation: a review of problems and solutions," Biomaterials (2001) 22(5):405-417.

Veronese et al., "PEGylation, successful approach to drug delivery," Drug Discov Today (2005) 10(21):1451-1458.

Wallace et al., "Increasing prevalence of gout and hyperuricemia over 10 years among older adults in a managed care population," J Rheumatol ( 2004) 31(8):1582-1587.

Wortmann and Kelley, Gout and hyperuricemia in: Ruddy, Harris, Sledge, Kelley (eds.), Kelley's Textbook of Rheumatology, 6th ed., (2001), pp. 1339-1376, W. B. Saunders Co., Philadelphia.

Wu et al., "Two independent mutational events in the loss of urate oxidase during hominoid evolution," J Mol Evol (1992) 34:78-84.

Wu et al., "Urate oxidase: primary structure and evolutionary implications," Proc Natl Acad Sci USA (1989) 86(23):9412-9416.

Yue et al., "Homology modeling and bioinformatics analysis of three-dimensional structure of human urate oxidase," Computers and Applied Chemistry (2007) 24(12):1643-1646.

Bayol et al., "Study of pH and temperature-induced transitions in urate oxidase (Uox-EC1.7.3.3) by microcalorimetry (DSC), size exclusion chromatography (SEC) and enzymatic activity experiments," Biophys Chem (1995) 54(3):229-235.

Chen et al., "The epidemiology study of hyperuricemia and gout in a community population of Huangpu District in Shanghai," Chin Med J (Engl) (1998) 111(3):228-230.

Database accession No. EMBL:AAW65996, "*Canis lupus* familiaris (dog) urate oxidase," dated Jan. 31, 2005, retrieved from EBI online on Sep. 26, 2014, 2 pages.

Emmerson, "The management of gout," N Engl J Med (1996) 334(7):445-451.

Extended European Search Report for European Patent Application No. 10825963.1, dated Aug. 16, 2013, 6 pages.

Huang and Wu, "Modified colorimetric assay for uricase activity and a screen for mutant *Bacillus subtilis* uricase genes following StEP mutagenesis," Eur J Biochem (2004) 271 (3):517-523.

International Preliminary Report on Patentability and Written Opinion for PCT/CN2010/071020, dated May 1, 2012, 17 pages (English translation attached).

International Search Report for PCT/CN2010/071020, mailed Jul. 15, 2010, 16 pages (English translation attached).

Jones et al., "Renal dysfunction and hyperuricemia at presentation and relapse of acute lymphoblastic leukemia," Med Pediatr Oncol (1990) 18(4):283-286.

Pui et al., "Urate oxidase in prevention and treatment of hyperuricemia associated with lymphoid malignancies," Leukemia (1997) 11(11):1813-1816.

Retailleau et al., "Complexed and ligand-free high-resolution structures of urate oxidase (Uox) from *Aspergillus flavus*: a reassignment of the active-site binding mode," Acta Crystallogr D Biol Crystallogr (2004) 60(Pt 3):453-462.

Suzuki et al., "Molecular cloning and expression of uricase gene from *Arthrobacter globiformis* in *Escherichia coli* and characterization of the gene product," J Biosci Bioeng (2004) 98(3):153-158.

Zhang et al., "Structure-based characterization of canine-human chimeric uricases and its evolutionary implications," Biochimie (2012) 94(6):1412-1420.

Restriction Requirement in U.S. Appl. No. 13/504,065, dated Aug. 6, 2013, 8 pages.

Response to Restriction Requirement in U.S. Appl. No. 13/504,065, dated Aug. 27, 2013, 9 pages.

Third Preliminary Amendment in U.S. Appl. No. 13/504,065, dated Sep. 23, 2013, 6 pages.

Notice of Allowance in U.S. Appl. No. 13/504,065, dated Oct. 2, 2013, 9 pages.

| No. | Amino Acid | No. | Amino Acid |
|---|---|---|---|
| 1 | M | 2 | Y |
| 3 | x | 4 | N |
| 5 | D | 6 | E |
| 7 | V | 8 | E |
| 9 | F | 10 | V |
| 11 | R | 12 | T |
| 13 | G | 14 | Y |
| 15 | G | 16 | K |
| 17 | D | 18 | M |
| 19 | V | 20 | K |
| 21 | V | 22 | L |
| 23 | H | 24 | I |
| 25 | Q | 26 | R |
| 27 | D | 28 | G |
| 29 | x | 30 | Y |

| Results | |
|---|---|
| Note | NH₂-M-Y-x-N-D-E-V-E-P-V-R-T-G-K-D-M-V-K-V-L-H-I-Q-R-D-G-x-Y (

PEGYLATED ANALOGUE PROTEIN OR CANINE URATE OXIDASE, PREPARATION METHOD AND USE THEREOF

CROSS-REFERENCE TO RELATED APPLICATIONS

This application is the national phase of PCT application PCT/CN2012/071106 having an international filing date of Feb. 14, 2012, which claims priority to Chinese Patent Application No. 201110037301.8, filed on Feb. 14, 2011. The contents of the above-listed applications are incorporated herein by this reference in their entireties.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 717412000400SeqList.txt, date recorded: Oct. 16, 2013, size: 16,525 bytes).

TECHNICAL FIELD

The present invention relates to biotechnology and pharmaceuticals. More specifically, the present invention relates to a PEGylated analogue protein of canine urate oxidase that may be administrated in multiple replications with high enzyme activity retention rate, low immunogenicity, and long half-life; as well as preparation method and use thereof.

This application claims priority to the Chinese Patent Application No. 201110037301.8, filed Feb. 14, 2011, the disclosure of which is herein incorporated by reference in its entirety.

BACKGROUND

Hyperuricemia is a disease from excessive purine metabolism. Uric acid, the final product of purine metabolism in human bodies, may cause hyperuricemia at a concentration of over 70 mg/L. Depending on its pathogenesis and duration, hyperuricemia may be further classified to acute hyperuricemia and chronic hyperuricemia. Acute hyperuricemia is a common complication in hematologic tumors and treatment therefor. With radio- and chemotherapy against hematologic tumors, urate concentration in vivo may be dramatically elevated by increased cytolysis and purine metabolite release, leading to acute hyperuricemia as well as renal failure in severe cases (Hershfield M S., Cecil Textbook of Medicine ($20^{th}$), 1508-1515). Hematologic tumor is one of the diseases severely imparing human healths, and common hematologic tumors mainly include various kinds of leukemia, multiple myeloma and malignant lymphoma. As a metabolic disease, chronic hyperuricemia is caused by human purine metabolism disorder in vivo, and is likely to further develop into gout, an acute or chronic disease from the crystallization and precipitation of urates in soft tissues. The major clinical manifestations of gout are repeated attacks of arthritis and/or nephropathia; and meanwhile, with long-term elevation of blood uric acid level, uric acid may be crystallized and precipitated in connective tissues and results in formation of granuloma, which gradually becomes tophus (Nancy J G, Susan J K, Edna S, John S S et al., *Arthritis Res Ther.*, 2005, 8 (1): R12). In the last 20 years, with the improvement of human living standards, the prevalence rate of chronic hyperuricemia/gout rises constantly. An epidemiology survey in England showed that the prevalence rate of gout rises from 1.19% in 1990 to 1.4% in 1999 (Wallace K, Riedel A, Joseph-Ridge N, Wortmann R., J. Rheumatol., 2004, 31: 1582-1587). Another survey in coastal areas of Shandong province, China, in 2008 showed that patients with hyperuricemia take 13.19% part of the total population, whereas patients with gout take 1.14% (Miao Z, Li C, Chen Y, et al., J Rheumatol., 2008; 35: 1859-1864). Therefore, such a disease has become an important one that jeopardizes human health.

Substantially, hyperuricemia is associated with urate oxidase gene mutation and deactivation during human evolutions, wherein a terminator codon is introduced in advance to the coding sequence of urate oxidase (Wu X, Lee C C, Muzny D M, Caskey C T., Proc Natl Acad Sci USA, 1989, 86: 9412-9416), thus disabling the synthesis of active urate oxidase and terminating human purine catabolism at uric acid (Wu X, Muzny D M, Lee C C, Caskey C T., J Mol Evol., 1992, 34: 78-84). Urates with lower solubility (~11 mg/dl) can be transformed to more soluble allantoin (~147 mg/dl) by active urate oxidase in liver peroxisomes of non-human primates and other mammals, hence being more effectively excreted by kidney (Wortmann R L, Kelley W N, *Kelley's Textbook of Rheumatology* (6th), 2001: 1339-1376). On worldwide market, urate oxidase pharmaceuticals include Rasburicase, a recombinant urate oxidase derived from *Aspergillus flavus*, by Sanofi Inc., France, granted by FDA in 2002 (Bosly A, Sonet A, Pinkerton C R, McCowage G, Bron D, Sanz M A, Van den Berg H., Cancer, 2003, 98: 1048-54). Rasburicase is prepared by *Saccharomyces cerevisiae* fermentation and purification, and may be used in short-term treatment of severe hyperuricemia from chemotherapy against tumor with better effect than that of allopurinol. However, because the urate oxidase derived from *Aspergillus flavus* shares a homology of lower than 40% with that from human (Lee C C, Wu X, Gibbs R A, Cook R G Muzny D M, Caskey C T., Science, 1988, 239: 1288-1291), antibodies thereagainst will be generated in vivo in 70% of patients after multiple dosing, thus leading to a rapid decrease of urate oxidase effects as well as severe allergy reactions (Navolanic P M, Pui C-H, Larson R A, et al., Leukemia, 2003, 17: 499-514).

Covalent modification with polyethelene glycol (PEG) has been proved to be useful to decrease protein immunogenicity, increase protein solubility and extend the half-life (Veronese F M, Pasut G, Drug Discov. Today, 2005, 10: 1451-458). Various PEGylated recombinant protein drugs have been granted by FDA at present. To conjugate to a target molecule, PEG needs to be activated at one end or two with a selected functional group, depending on characteristics of molecules to be conjugated. A linking group for PEG covalent modification of protein may be any one of biocompatible linking groups. Common biocompatible linking groups include ester, amido, imido, urethane, succinimidyl (e.g., succinimidyl succinate (SS), succinimidyl propionate (SPA), succinimidyl carboxymethyl (SCM), succinimidyl succinamide (SSA) or N-hydroxyl-succinimidyl (NHS)), epoxyl, oxycarbonyl imidazolyl, nitrophenyl group (e.g., nitrophenyl carbonate (NPC) or trichlorobenzene carbonate (TPC)), and histidinyl or primary amine. Theoretically, the activated PEG may be reacted with main amino acids (e.g., Lys, Cys, His, Asp, Glu, Ser, and Thr, etc.) in a protein at the N-terminus or C-terminus, in which a reaction with Lys at the N-terminus is most commonly used.

PEGylated urate oxidase was studied since the late 1970s. A urate oxidase derived from *Candida* was modified with cyanuric chloride activated 5 kDa PEG by Nihimura and Tsuji et al. However, with modification rates of up to 20%~30%, both enzyme activity and retention rate decrease to less than 50%, and immunogenicity is failed to be decreased with sufficient retention on enzyme activity (Nishimura H, Ashihara Y, Matsushima A, Inada Y., Enzyme, 1979, 24: 261-264; Tsuji J-1, Hirose K, Kashara E, Naitoh M, Yamamoto I., Int J. Immunopharmacol., 1985, 7: 725-730). Previously, PEGylated urate oxidase was studied on reaction in human body. A urate oxidase derived from *Candida* was modified with a 5 kDa PEG by Davis et al. After the conjugate was injected into 5 subjects, the urate oxidase concentration in the serum decreased to be undetectable. 4 weeks later, another injection resulted also in undetectable urate oxidase antibodies, as detected by gel diffusion method that is not so sensitive (Davis F F, Abuchowshi A, Karp D., J Pharmacol Exp Ther., 1981, 219: 352-354). From the foregoing, the PEGylated urate oxidase is safe and effective in human body. However, there are problems on long-term security and effectiveness, owing to high antigenicity of urate oxidase and deficiency in PEG agents.

With the appearance of the second generation of branch-chained PEG with high molecular weight, PEGylated urate oxidase was studied again. A recombinant swine-gelada urate oxidase was modified with 10 kDa mPEG-NPC at Lys residue by Duke University and Savient Inc. (Pegloticase) (Michael H, Susan J. K., 2006, U.S. Pat. No. 7,056,713B1). With each subunit conjugated with 9 PEGs, the enzyme activity may be retained by more than 75%, and the immunogenicity is substantially eliminated as verified by animal experiments. (Sherman M R, Saifer M G, Perez-Ruiz F., Adv Drug Deliv Rev., 2008, 60: 59-68). Pegloticase has been granted by FDA at Sep. 14, 2010 for long-term treatment (6 months) of refractory gout. However, antibodies against Pegloticase occur in 90% of clinical tests, and the drug is only suitable for intravenous injection. Because of the potential immunogenicity and inconveniency for administration, long-term treatment obedience in patients with chronic gout is decreased.

Drug development on PEGylated urate oxidase was also carried out by Phoenix Inc. (Ensor C M, Clark M A, Holtsberg F W., 2005, U.S. Pat. No. 6,913,915B2), the urate oxidase modified by whom is a *Candida* urate oxidase, with preferred PEG as mPEG-SC and mPEG-SPA with an average molecular weight of 20 KD, and modified site as the same Lys residue. Each protein was conjugated with 18~22 PEG chains. The modified urate oxidase retains 75% of activity with a half-life of up to 3 days in mice body, far longer than that of non-modified urate oxidase, namely, 4 hours (Bomalaski J S, Holtsberg F W, Ensor C M, Clark M A., J Rheumatol., 2002, 29: 1942-1949). Said PEGylated urate oxidase was studied clinically at 2001. However, phase I clinical trial showed that the efficacy is weakened after administration, and thus the research was terminated (Bolmalaski J S, Goddard D H, Grezlak D, et al., Arthritis Rheum., 2002, 46: S141).

So far, there is worldwidely no commercialized urate oxidase product that has an appropriate half-life and may be used in long-term treatment with security and no immunogenicity. Although the human urate oxidase has become a pseudogene because of the mutation and loss of activity, the immunogenicity of the enzyme would be reduced if the gene was reformed and the activity was recovered. However, because of missense mutations accumulated during the evolution due to the lack of selective pressure, it is difficult to find out and correct all mutations and recover the human uricase activity. Because of the high activity of microorganism urate oxidases and the low immunogenicity of mammal urate oxidases, the two urate oxidases are studied for long-term use of urate oxidase at now. Though PEGylation may decrease the immunogenicity of microorganism derived urate oxidase, the immunoreaction is not effectively eliminated in human bodies. Clinical research on long-term treatment of chronic gout with the PEGylated recombinant microorganism urate oxidase has been stopped in foreign countries (such as in Phenix Inc. and Enzon Inc.). In contrast, in mammal urate oxidase studies, PEGylated swine urate oxidase from Duke University and Savient Inc. has successfully come into market, indicating that protein homology is still a key element for the immunogenicity of PEGylated proteins. To further improve the protein homology of urate oxidase, the inventor has carried out a study on human-canine chimeric urate oxidase on the basis of canine urate oxidase, which exhibits higher homology to humanized urate oxidase and greater specific activity, for which a Chinese patent application (No. 200910191240.3) and a PCT application (No. PCT/CN2010/071020) have been filed, respectively. PEGylation on the basis of the above canine urate oxidase analogue is studied in the present invention for a new and long-acting recombinant urate oxidase, which, as retaining high enzymatic activity, may be possessed with extended half-life and decreased immunogenicity in vivo for the treatment of acute hyperuricemia from chemotherapy against tumors and hyperuricemia or chronic gout from metabolic disorders.

DETAILS OF THE INVENTION

One aim of the invention is to provide a new PEGylated analogue protein of canine urate oxidase. Said analogue protein of canine urate oxidase may be a canine urate oxidase protein, or a chimeric protein comprising part of the amino acid sequence of a canine urate oxidase and part of the amino acid sequence of a human urate oxidase, or a mutant protein thereof. The average molecular weight of said PEG is about 1 kD~40 kD, and one monomer urate oxidase is conjugated in average with 2~15 PEG molecules.

Another aim of the invention is to provide a method for the preparation of said PEGylated analogue protein of canine urate oxidase. The method includes: preparing an analogue protein of canine urate oxidase comprising more than 95.0% of tetramer urate oxidase protein; PEGylating said analogue protein of canine urate oxidase; and purifying said modified protein.

Another aim of the invention is to provide a pharmaceutical composition of PEGylated analogue protein of canine urate oxidase for the prevention and/or treatment of acute hyperuricemia caused by chemotherapy against hematologic tumors, metabolic disorder or chronic gout. Said pharmaceutical composition comprises effective dose of PEGylated analogue protein of canine urate oxidase as an effective constituent, and may further comprise pharmaceutically acceptable carriers and excipients.

Another aim of the invention is to provide use of the above PEGylated analogue protein of canine urate oxidase. Said protein may be used for the prevention and/or treatment of acute hyperuricemia caused by chemotherapy against hematologic tumors, metabolic disorder or chronic gout.

Therefore, in the first aspect of the invention, the invention provides a PEGylated analogue protein of canine urate oxidase (Said analogue proteins of canine urate oxidase of the invention are all derived from Chinese Patent Application No. 200910191240.3), including non-mutated canine urate oxidase protein (SEQ ID No:1); or a chimeric protein comprising part of the amino acid sequence of a canine urate oxidase and part of the amino acid sequence of a human urate oxidase; or a mutant protein thereof. Wherein, the first 240 amino acids at the N-terminus of said chimeric protein may be amino acids 1-240 of canine urate oxidase; and the following 64 amino acids are amino acids 241-304 of human urate oxidase (SEQ ID No:2). The PEGylated analogue protein of canine urate oxidase of the invention may be a mutant protein with substitution, deletion or addition of one or several amino acids in canine urate oxidase or the above chimeric protein, while remaining the same activity. Said mutant protein of the chimeric protein comprising part of the amino acid sequence of a canine urate oxidase and part of the amino acid sequence of a human urate oxidase includes, but is not limited to at least one of the following mutant proteins (presented in triplet form of letter-number-letter, wherein numbers represent the location of amino acids mutated, the former letter refers to the original amino acid, and the latter refers to the amino acid substituting the former) with mutations at 2-5 of positions: S246T-S248G-R249Q (SEQ ID No: 3), and L245H-A252E-I253M (SEQ ID No: 4). The above canine urate oxidase protein, the chimeric protein comprising part of the amino acid sequence of a canine urate oxidase and part of the amino acid sequence of a human urate oxidase, and mutant proteins thereof may be trunctated by 1-9 amino acids at the N-terminus (as in SEQ ID No: 5), and by 1-3 amino acids at the C-terminus (as in SEQ ID No: 6).

In the present invention, PEGylation sites of said analogue protein of canine urate oxidase include, but are not limited to the N-terminal α-amino and/or the ε-amino on Lys residue of the urate oxidase protein. Preferably, the PEGylation site is the ε-amino on Lys residue. Said analogue protein of canine urate oxidase is covalently linked to the active group of PEG via amino ester, secondary amine or amide linkages And preferably, said analogue protein of canine urate oxidase is covalently linked to the active group of PEG via a covalent linkage. Prior to the PEGylation of said analogue protein of canine urate oxidase, PEG needs to be activated. Active groups linked at one end of PEG for the activation include, but are not limited to succinimidyl, nitrophenyl, amido, imido, carbamate, aldehyde, and histidinyl groups. Preferably, the linked active group is a succinimidyl or nitrophenyl group. And more preferably, the linked active group is a succinimidyl propionate (SPA) or nitrophenyl carbonate (NPC) group, in other words, said analogue protein of canine urate oxidase is covalently linked to PEG via succinimidyl propionate (SPA). Blocking groups linked at the other end of PEG in the activation include, but are not limited to monomethoxy, ethoxy, propoxy, butoxy; galactose or dextrose etc. And preferably, the linked blocking group is a monomethoxy. The above PEG may be branch-chained or linear-chained. And preferably, the PEG is linear-chained. The average molecular weight of PEG is about 1 kDa~40 kDa. Preferably, the average molecular weight of PEG is 5 kDa~20 kDa. And more preferably, the average molecular weight of PEG is 5 kDa. Each monomer of the analogue protein of canine urate oxidase conjugates in average with 2~15 PEG molecules. Preferably, each monomer of the analogue protein of canine urate oxidase conjugates in average with 4~12 PEG chains. And more preferably, each monomer of the analogue protein of canine urate oxidase conjugates in average with 6~11 PEG chains.

In the second aspect of the invention, the invention provides a method for the preparation of said PEGylated analogue protein of canine urate oxidase, said method including:
 a. preparing a urate oxidase protein containing more than 95.0% of tetramer analogue protein of canine urate oxidase prior to the PEGylation;
 b. PEGylating said analogue protein of canine urate oxidase; and
 c. separating and purifying said modified protein.

Wherein, in said step a, methods for the preparation of analogue protein of canine urate oxidase prior to the PEGylation include molecular sieve chromatography and ion exchange chromatography. And preferably, anion exchange chromatography is used for the preparation of said analogue protein of canine urate oxidase.

In said step b, while PEGylating said analogue protein of canine urate oxidase, namely, conjugating PEG with the analogue protein of canine urate oxidase, the molar ratio of said analogue protein of canine urate oxidase to PEGylating agent is 1:40~1:200. And preferably, the molar ratio is 1:120~1:160. A carbonate buffer solution is employed in the conjugation system, wherein pH ranges from 8.0~11.0, preferably 9.5~10.5, and ion strength ranges from 10~200 mmol/L, preferably 50~150 mmol/L, in said carbonate buffer.

In said step c, chromatography and/or ultrafiltration are employed for the separation and purification of said PEGylated analogue protein of canine urate oxidase. Methods for the separation and purification include, but are not limited to, molecular sieve chromatography, ion exchange chromatography, hydrophobic chromatography, and tangential flow ultrafiltration. Preferably, said method for the separation and purification of PEGylated analogue protein of canine urate oxidase is molecular sieve chromatography.

In the third aspect of the invention, the invention provides a pharmaceutical composition of the PEGylated analogue protein of canine urate oxidase. The pharmaceutical composition comprises effective dose of PEGylated analogue protein of canine urate oxidase as an effective constituent, and may further comprise pharmaceutically acceptable carriers and excipients. Said composition may be used for the prevention and/or treatment of acute hyperuricemia from chemotherapy against hematologic tumors and hyperuricemia or chronic gout from metabolic disorders. Said hematologic tumors include, but are not limited to, leukemia, multiple myeloma and malignant lymphoma. The main symptoms of said hyperuricemia and chronic gout include, but are not limited to, uric acid nephropathy and gouty arthritis. Administration routes for said pharmaceutical composition include, but are not limited to, intravenous injection, subcutaneous injection, intramuscular injection, and intraperitoneal injection, or inhalation of aerosol preparation. Preferably, the administration route of said pharmaceutical composition is intravenous injection or subcutaneous injection.

In the fourth aspect of the invention, the invention provides use of the above PEGylated analogue protein of canine urate oxidase on preparing drugs for the prevention and/or treatment of acute hyperuricemia from chemotherapy against hematologic tumors and hyperuricemia or chronic gout from metabolic disorders.

In the present invention, the molecular weight of non-PEGylated tetramer urate oxidase protein is usually 140 kDa, whereas the immune system in vivo may be effectively activated by a protein with molecular weight of more than 100 kDa. A 20 kDa mPEGylated Candida-derived urate oxidase developed by Phenix Inc. failed in phase I clinical trial because of its high immunogenicity (Bolmalaski J S, Goddard D H, Grezlak D, et al., Arthritis Rheum., 2002, 46: S141). Pegloticase, a drug already on the market, is a 10 kDa mPEGylated protein with molecular weight of 540 kDa (Sherman M R, Saifer M G, Perez-Ruiz F., Adv Drug Deliv Rev., 2008, 60: 59-68), resulting in possibility of high immunogenicity in clinical stage. Meanwhile, antibodies produced against Pegloticase injection targets mainly at the PEG part. Therefore, by utilizing mPEG with smaller molecular weight of 5 kDa, the production of antibodies against the PEG part, and hence the immunogenicity of the entire PEGylated urate oxidase, may be decreased. Pegloticase had failed in phase I clinical trial with subcutaneous injection because of the slow release and stimulus response at the site of injection. Therefore, subcutaneous injection of Pegloticase was abandoned by Savient Inc. (Ganson N J, Kelly S J, Scarlett E, Sundy J S, Hershfield M S., Arthritis Res Ther., 2006, 8: R12). With a smaller mPEGylation of 5 kDa, drugs may be absorbed more rapidly with less stimulus response and enhanced bioavailability at the site of subcutaneous injection. Therefore, in a specific embodiment of the invention, the 5 kDa mPEG, which has already been used in many PEGylated protein drugs on the market, is employed for the modification of canine urate oxidase analogue.

The active urate oxidase is a tetramer protein, and about ⅓ amino acids in urate oxidase protein family are highly hydrophobic (Colloc'h N, Poupon A, Mornon J P., Proteins, 2000, 39: 142-154). Therefore, an octamer or larger polymers are theoretically easy to form between the tetramer proteins. An octamer form of microorganism urate oxidase has been published in an X-ray crystallography experiment (Retailleau P, Colloc'h N, Civares D, et al., Acta Crystallogr., Sect. D. 2005, 61:218-229). Experts in FDA believe that a molecule with over 100 kDa of molecular weight tends to induce immunoreactions (Rosenberg, A S., AAPS J., 2006, 8: E501-507), while the molecular weight of tetramer urate oxidase protein is up to 140 kDa, and non-modified urate oxidase polymers will be of higher immunogenicity. The inventor had tried methods, such as phenyl or butyl hydrophobic interaction chromatography and xanthine affinity chromatography, etc., for the separation of analogue protein of canine urate oxidase from different forms of polymers, but all failed, indicating no significant hydrophobic difference existing between the active urate oxidase tetramer and polymers. The polymer is not caused by hydrophobic aggregation, and the above polymers are all active forms of urate oxidase. The inventor also tested ion-exchange chromatography, and in a preferred embodiment of the invention, different forms of analogue protein of canine urate oxidase are effectively separated with high resolution Source 15Q, wherein the ion strength needed for the elution of tetramer urate oxidase protein is lower than that for polymers. The result shows that, under same buffered conditions, some basic amino acids are concealed in the aggregated polymers of analogue protein of canine urate oxidase, shifting down isoelectric point thereof with negative charges more than the tetramer protein under same basic environments. More preferably, the content of tetramer urate oxidase prepared with anion exchange chromatography on the basis of different characteristics of non-modified tetramer and polymer urate oxidases is over 95.0%.

The bottleneck problem in the development of 5 kDa PEGylated urate oxidase is the rapid decrease of enzyme activity with the modification of the protein, thus losing the effectiveness (Chen R H, Abuchowski A, Van Es T, Palczuk N C, Davis F E, Biocheim Biophys Acta., 1981, 660: 293-298). The inventor finds that, a 5 kDa PEGylated urate oxidase with tetramer urate oxidase content of over 95.0% may retain enzyme activity retention rate of more than 85%. In one specific embodiment of the invention, the inventor makes a comparison of enzyme activity retention between modified tetramers with different polymer contents. A urate oxidase protein with tetramer urate oxidase content of 10.8% is modified with enzyme activity retention rate of merely 71.7%, whereas the urate oxidase protein with tetramer urate oxidase content of over 95.0% is modified with an enzyme activity retention rate of over 85.0%, indicating that the increase of polymer urate oxidase protein content is the reason for the loss of the activity of a 5 kDa PEGylated urate oxidase. The separation of polymer urate oxidase may not only eliminate the potential immunogenicity, but also increase the 5 kDa PEGylated enzyme activity retention rate, thus solving the bottleneck problem in the development of 5 kDa PEGylated urate oxidase.

Protein PEGylations generally include N-terminal α-amino modification, Lys ε-amino modification, Cys sulfydryl modification, and C-terminal carboxyl modification, etc. However, with a molecular weight of up to 140 kDa, the active tetramer urate oxidase protein may not be modified with decreased immunogenicity on the usual N- or C-terminal sites as in other hormones and cytokines. Furthermore, there are only 4 free sulfydryls on the analogue protein of canine urate oxidase, and thus each monomer may theoretically be conjugated with only 4 PEG molecules at most, still not fulfilling the requirement. Therefore, modifications have to be performed in a non-fixed-point way at lysines of the analogue protein of canine urate oxidase. In one embodiment of the aspect of the invention, canine urate oxidase analogues with different modification ratios are used to immune mice, wherein the non-modified protein immunogenicity is decreased effectively only when each monomer is conjugated with more than 6 PEGs. More preferably, each urate oxidase monomer is conjugated with 6~11 PEG chains.

Usually, PEG is linked to Lys amino in urate oxidase protein via amino ester, secondary amine or amide linkage. More preferably, PEG is covalently linked to the protein via succinimides. Said succinimides include, but is not limited to succinimidyl succinate (SS), succinimidyl carbonate (SC), succinimidyl propionate (SPA), succinimidyl butyrate (SBA), succinimidyl formate (SCM), succinimidyl succinamide (SSA) or N-hydroxyl-succinimide (NHS). Succinimidyl propionate (SPA) exhibits better stability and connective efficiency in aqueous solution, as compared to succinimidyl carbonate (SC), succinimidyl succinamide (SSA) and N-hydroxyl-succinimide (NHS), etc., forming an active group of succinimidyl propionate in the PEG activation. In a preferred embodiment of the invention, the Lys ε-amino of the analogue protein of canine urate oxidase is covalent linked to a 5 kDa PEG via succinimidyl propionate.

PEG is derived from the anion ring opening polymerization of oxirane that is electrophilically attacked at hydroxyl ion thereof (Roberts M J, Bentley M D, Harris J M., Adv Drug Deliv Rev., 2002, 54: 459-476), leaving hydroxy group at both ends. If not being blocked at one end, both ends may be coupled with active groups in further activations, resulting in a bifunctional modification agent that leads to conjugates comprising two or more proteins and additional immunogenicities due to the enlarged molecular weight (Veronese F M., Biomaterials, 2001, 22: 405-417). With hydroxyl group at one end blocked, the most commonly used monomethoxy PEG (mPEG) may be obtained for protein modification, and the non-blocked hydroxyl group on the other end may react with different active groups to further modify different groups in the protein molecule. In a specific embodiment of the invention, PEGs are all single-functional with one end blocked. Blocking groups linked on PEG include, but are not limited to monomethoxy, ethoxy, propoxy, butoxy, galactose or dextrose, etc. In a preferred embodiment of the aspect of the invention, the blocking group for PEG is a monomethoxy that has been used in multiple PEGylated protein drugs on the market with verified security.

The pH value for protein PEGylation with succinimidyl propionate as an active group usually ranges from 7.0 to 9.0 (Roberts M J, Bentley M D, Harris J M., Adv Drug Deliv Rev., 2002, 54: 459-476). To further improve the solubility of the canine urate oxidase analogue and increase the number of Lys residues to be modified thereon, as well as to enhance the specificity of modification, in a preferred embodiment of the invention, the pH value is adjusted to 9.0~11.0, which leads to a specific conjugation of PEG with the Lys ε-amino of the analogue protein of canine urate oxidase with no reaction to the N-terminal α-amino thereof. More preferably, pH value of the modification ranges from 9.5 to 10.5. Conjugation buffer systems commonly used in said pH range include, but are not limited to those of phosphate buffer, Tris-HCl buffer and carbonate buffer solution. To further maintain the solubility of the analogue protein of canine urate oxidase, in a preferred embodiment of the invention, carbonate is selected for the conjugation buffer system. Concentrations commonly used for carbonate buffer solution range from 10 to 200 mmol/L. To increase the modification efficiency of the 5 kDa PEG, in a preferred embodiment of the invention, 50~150 mmol/L is selected as the working concentration of carbonate buffer. To further increase the number of PEGs conjugated to the analogue protein of canine urate oxidase, the molar ratio of the analogue protein of canine urate oxidase to PEG is from 1:40 to 1:160 during conjugation. More preferably, the molar ratio of the analogue protein of canine urate oxidase to PEG is from 1:120 to 1:160.

In the present invention, purification methods commonly used for modified protein include, but are not limited to molecular sieve chromatography, ion exchange chromatography, hydrophobic chromatography, and tangential flow ultrafiltration. The inventor finds that, as compared with non-modified protein, the 5 kD PEGylation in multiple sites not only effectively decreases the immunogenicity, but also covers up the ionicity and hydrophobicity of the analogue protein of canine urate oxidase, thus making it hardly to be connected with routine loading materials for ion exchange chromatography, hydrophobic chromatography and reverse phase interaction. In a preferred embodiment of the aspect of the invention, molecular sieve chromatography may be used to effectively separate modified protein from non-modified proteins and by-product of the modification. The modified analogue protein of canine urate oxidase purified by such a method has a purity of over 99.0%, as determined by RP-HPLC and SEC-HPLC.

Pharmaceutical preparations with said PEGylated analogue protein of canine urate oxidase of the invention as an effective constituent may comprise, but are not limited to, diluents, stabilizers, preservatives, solvents, emulsifiers, adjuvants and carriers, etc., wherein, 1) diluents: buffers of phosphate, acetate Tris-HCl, etc.; 2) pH value and ion strength; 3) detergents and solvents: sorbitol, Tween-20, Tween-80; 4) fillers: lactose, dextrose, sucrose, mannitol. An effective dose of the effective constituent refers to the dose for effective treatment or prevention with consideration of apparent molecular weight, patients' body weight or age, etc. In a preferred embodiment of the invention, the preparation employs diluents of 10~20 mM, pH 7.4~9.0; solvents of 0.004%~0.04% of Tween –20; and fillers of 4%~5% of mannitol.

Administration routes of said pharmaceutical composition of the PEGylated analogue protein of canine urate oxidase of the invention include, but are not limited to intravenous injection, subcutaneous injection, intramuscular injection and intraperitoneal injection or inhalation aerosol preparations. In a preferred embodiment of the invention, the in vivo injection of 5 kDa PEGylated analogue protein of canine urate oxidase into cynomolgus monkey, which shares greater homology with human, may result in an elimination half-time of up to 134.3 h, indicating that the injection thereof into a human body may also result in an elimination half-time of more than 1 week, thus facilitating injection in every 1~2 weeks as desired. Moreover, the bioavailability of the subcutaneous injection is over 60%, suggesting the subcutaneous injection as a route to be selected in human beings, which will improve the obedience for long-term treatment.

Said pharmaceutical composition comprising PEGylated analogue protein of canine urate oxidase of the invention as an effective constituent may be used for the prevention and/or treatment of acute hyperuricemia from chemotherapy against hematologic tumors and hyperuricemia or chronic gout from metabolic disorders. Said hematologic tumors include, but are not limited toleukemia, multiple myeloma and malignant lymphoma. The main symptoms of hyperuricemia and chronic gout include, but are not limited to uric acid nephropathy and gouty arthritis. An elevation on blood uric acid concentration is a basal characteristic for hyperuricemia diagnoses. In a preferred embodiment of the invention, normal chicken with the absence of urate oxidase and with uric acid as final product is used for the assessment of blood uric acid decrease by 5 kDa PEGylated analogue protein of canine urate oxidase. Results show that the blood uric acid concentration in normal chicken control group is constant at 220 μM; and with the injection of 5 kDa PEGylated analogue protein of canine urate oxidase, the blood uric acid concentration may be stabilized below 50 μM in 3~5 days, whereas the injection of non-modified analogue protein of canine urate oxidase decreases the blood uric acid concentration to merely about 130 μM in 1 day, then gradually back to normal. The 5 kDa PEGylated analogue protein of canine urate oxidase exhibits favourable effects on the decrease of blood uric acid concentration.

Uric acid nephropathy is a commonly encountered disease from hyperuricemia. In a preferred embodiment of the invention, a uric acid nephropathy animal model is successfully established with free feeding of yeast powder and injection of low concentration of sodium urate into rats, and the 5 kDa PEGylated analogue protein of canine urate oxidase is evaluated on the prevention of uric acid nephropathy. Results show that, the uric acid concentration in vivo in the treatment group may be stabilized below 80 μM with creatinine significantly decreased ($p<0.05$), indicating good protection effect for kidney injuries from hyperuricemia. Histopathology results show that, as compared to model control group, overall rating of the 5 kDa PEGylated analogue protein of canine urate oxidase groups are all significantly decreased ($p<0.001$), indicating significantly alleviated kidney injuries after drug administration. Therefore, the 5 kDa PEGylated analogue protein of canine urate oxidase exhibits good protection effect towards high kidney injuries from high level of uric acid in rats.

Gouty arthritis is another commonly encountered disease from hyperuricemia. By now, there is no animal model for the accurate assessment of gout drugs in the treatment of gouty arthritis. In a preferred embodiment of the invention, a gouty arthritis model is successfully established with injection of sodium urate crystal suspension into rabbit peripheral knee joint, and the 5 kDa PEGylated analogue protein of canine urate oxidase is evaluated on the treatment of gouty arthritis. Results show that, after the injection of sodium urate crystal, the model animal exhibits significant joint swelling with maximum at 6 h, which is recovered to the extent as in blank control group at 24 h after the administration, indicating that injection of the 5 kDa PEGylated analogue protein of canine urate oxidase may significantly decrease joint swelling from sodium urate crystals.

As compared with non-modified urate oxidase proteins, the 5 kDa PEGylated analogue protein of canine urate oxidase of the invention exhibits lower immunogenicity and better stability. As compared with PEGylated microorganism urate oxidase proteins, it exhibits lower potential immunogenicity. Also, as compared with other 10~20 kDa PEGylated analogue proteins of canine urate oxidase, it exhibits higher bioavailability and lower immunogenicity in subcutaneous injection. The PEG preparation method provided herein may further improve the enzyme activity retention rate of modified urate oxidase protein, the site specificity and homogeneity in modification, and the purity of the modified protein. Pharmaceutical compositions provided herein may effectively decrease blood uric acid concentration, prevent uric acid nephropathy, and treat gouty arthritis, and thus may be used for the prevention and/or treatment of acute hyperuricemia from chemotherapy against hematologic tumors and hyperuricemia or chronic gout from metabolic disorders.

The invention is described in details hitherto, and can be further illustrated with reference to the following examples, which are not meant to limit the present invention.

DESCRIPTION OF FIGURES

FIG. 4: N-terminal sequencing of PEGylated analogue protein of canine urate oxidase (SEQ ID NO:7)

EMBODIMENTS

EXAMPLE 1

PEGylating Conditions of Analogue Protein of Canine Urate Oxidase

The analogue protein of canine urate oxidase involved in this example is a mutant protein of the chimeric protein comprising part of the amino acid sequence of a canine urate oxidase and part of the amino acid sequence of a human urate oxidase according to the Application No. 200910191240.3 (SEQ ID NO: 5, the same to all PEGylated analogue proteins of canine urate oxidase in the following examples) that is prepared by genetic engineering technology with over 95.0% of purity in SDS-PAGE and RP-HPLC.

Figure 1A:
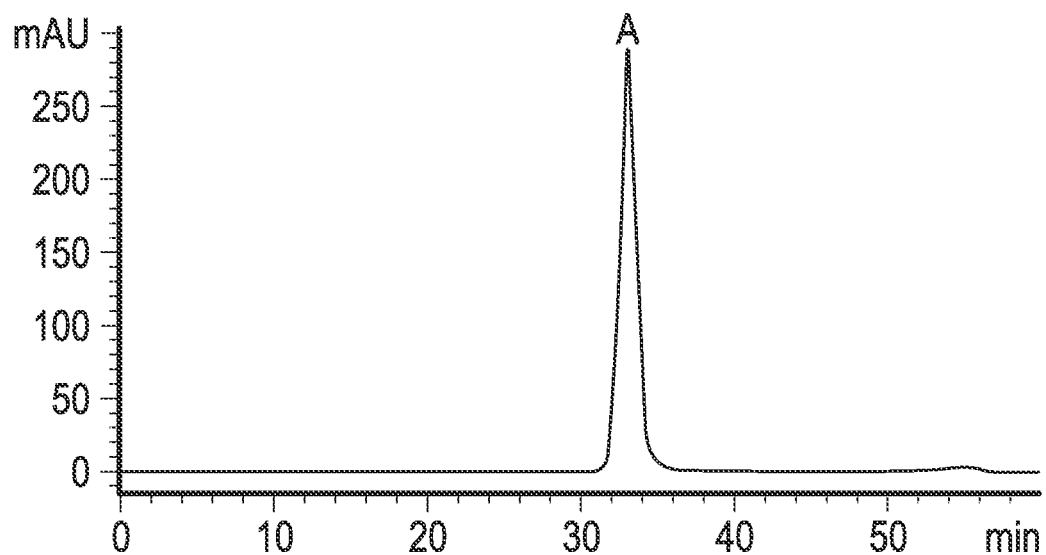
FIG. 1: SEC-HPLC assay on the analogue protein of canine urate oxidase prior to modification, wherein Fig. A shows that the tetramer urate oxidase protein content is over 95.0% in the 0.1 mmol/L NaCl eluent, Fig. B shows that the tetramer urate oxidase protein content is 14.5% in the 0.3 mmol/L NaCl eluent; wherein a refers to tetramer protein, b refers to octamer protein, and c refers to polymer protein.
Figure 1B:
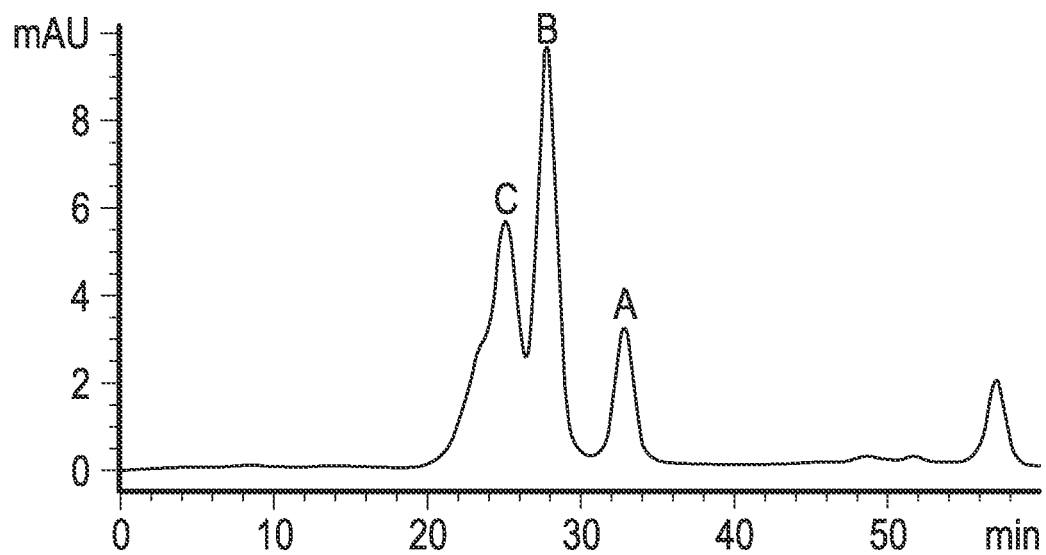

Source15Q anion exchange resin was prepared in column, washed with an elution buffer (2M NaCl, 0.2 mol/L $Na_2CO_3$—$NaHCO_3$ buffer, pH=10.3) for 5 column volumes, and balanced with a balanced solution (0.2 mol/L $Na_2CO_3$—$NaHCO_3$ buffer, pH=10.3). The above purified sample was loaded, balanced with the balanced solution and subject to gradient elution with an elution buffer comprising 0.1 mmol/L, 0.2 mmol/L, and 0.3 mmol/L NaCl. Absorption peaks were collected depending on the 280 nm absorbance and then subject to SEC-HPLC assays. As is shown in FIG. 1, the tetramer content is over 95.0% in the 0.1 mmol/L NaCl eluent, and the tetramer urate oxidase protein content is 14.5% in the 0.3 mmol/L NaCl eluent.

Figure 2:
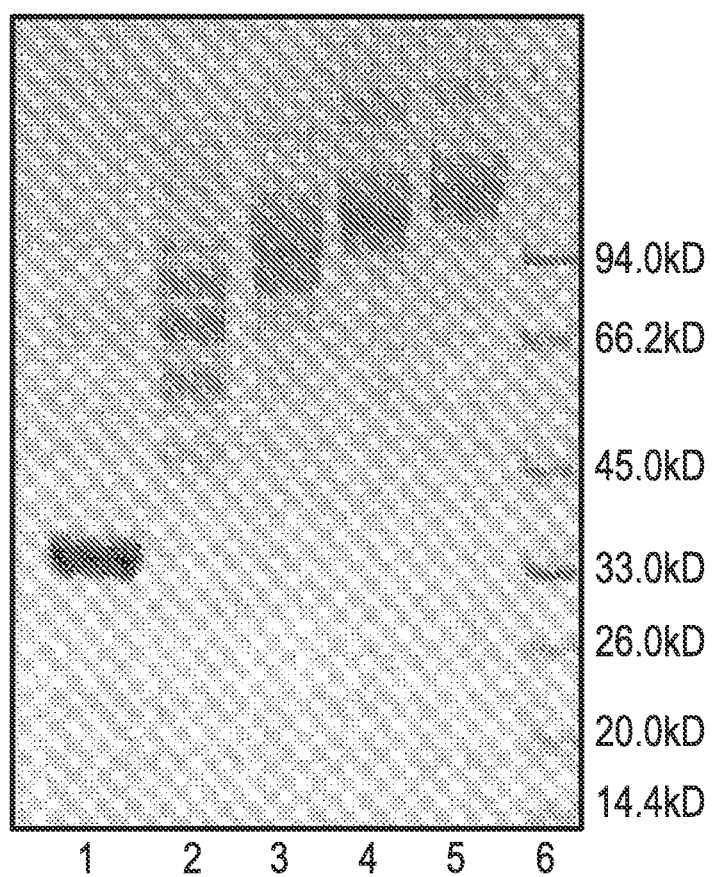
FIG. 2: SDS-PAGE of different ratio of PEGylated analogue protein of canine urate oxidase, wherein Lane 1 is non-modified protein, Lane 2 is 1:40 modified protein, Lane 3 is 1:80 modified protein, Lane 4 is 1:120 modified protein, Lane 5 is 1:160 modified protein, and Lane 6 is a protein marker; wherein PEGylated analogue protein of canine urate oxidase exhibits larger than theoretical values due to the slowed transport ratio.

The above purified tetramer analogue protein of canine urate oxidase was ultrafiltrated to 4.0 mg/ml, followed by the addition of 5 kDa mPEG-SPA dry powder (monomethoxy PEG succinimidyl propionate, purchased from JENKEM TECHNOLOGY CO., LTD, BEIJING) by molar ratios of 1:40, 1:80, 1:120 and 1:160 in 0.1 mol/L of $Na_2CO_3$—$NaHCO_3$ buffer, pH=10.3, to allow reactions for 4 hours at 4. Samples were taken respectively for SDS-PAGE to determine the PEGylation rate of analogue protein of canine urate oxidase. Results show that (see FIG. 2) each urate oxidase monomer may be conjugated to 2~6 of 5 kDa mPEGs at modification ratio of 1:40~1:80; and each urate oxidase monomer may be conjugated to 6~11 of 5 kDa mPEGs at modification ratio of 1:120~1:160.

Analogue proteins of canine urate oxidase with over 95.0% and 14.5% tetramer content were respectively ultrafiltrated to 4.0 mg/ml with the addition of 5 kDa mPEG-SPA dry powder by molar ratios of 1:120 in a 0.1 mol/L of $Na_2CO_3$—$NaHCO_3$ buffer, pH=10.3, to allow reactions for 4 hours at 4. Samples were taken respectively for enzyme activity retention rate assay to determine the effect of non-modified urate oxidase polymer protein on enzyme activity retention rate. Uric acid has a characteristic absorption peak at 292 nm, while the product has none, and different concentrations of uric acid correspond linearly to different absorptions. Therefore, with degradation by the urate oxidase, the decrease of uric acid absorbance at 292 nm was detected regularly to determine the enzyme activity as follows: 3 mL of 100 μM uric acid in borate buffer, pH=8.6, was pre-heated at 37 and added into a cuvette, with further addition of 10 μl of appropriately diluted enzymes, and the liquid was mixed. The change of absorbance at 292 nm was detected continuously, and concentrations of uric acid degradation was calculated according to the formular: C=A/εL (wherein, C refers to the uric acid concentration, A refers to absorbance at 292 nm, ε refers to the molar extinction coefficient of uric acid, and L refers to the optical length of the cuvette), and the enzyme activity was also calculated. One active unit (U) was defined as the enzyme amount being required to transform 1 μmol of uric acid to allantoin in one minute at 37 and pH 8.6. As is shown in Table 1, the modified analogue protein of canine urate oxidase with over 95.0% of tetramer urate oxidase protein content exhibits 87.7% of enzyme activity retention rate, whereas the modified analogue protein of canine urate oxidase with 14.5% of tetramer urate oxidase protein content exhibits only 71.7% of enzyme activity retention rate. That is to say, non-modified urate oxidase polymers may significantly decrease the enzyme activity retention rate of the 5 kDa PEGylated protein, and the enzyme activity retention rate may be over 85.0% by removing said polymers.

TABLE 1

|  | PEGylated analogue protein of canine urate oxidase-1 | PEGylated analogue protein of canine urate oxidase-2 |
| --- | --- | --- |
| Tetramer contents | >95.0% | 14.5% |
| Specific activities of non-modified protein | 11.3 | 9.2 |
| Specific activities of PEGylated protein | 9.9 | 6.6 |
| Enzyme activity retention rate after PEGylation | 87.7% | 71.7% |

EXAMPLE 2

Figure 3A:
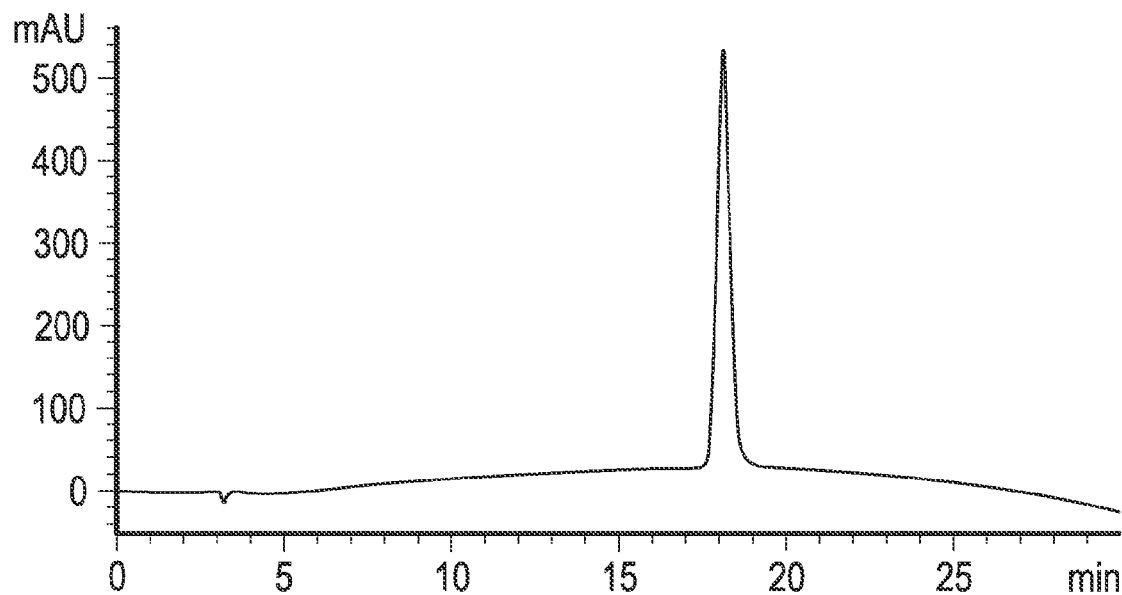
FIG. 3: Purity assay on PEGylated analogue protein of canine urate oxidase, wherein Fig. A represents RP-HPLC, Fig. B represents SEC-HPLC.
Figure 3B:
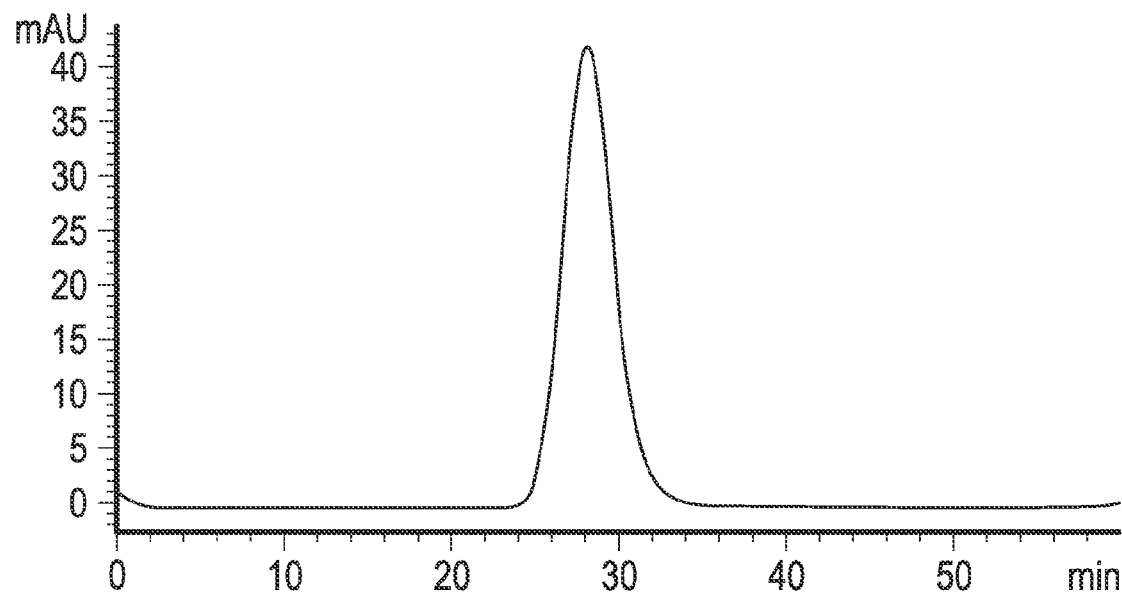

Separation and Purification of the PEGylated Analogue Protein of Canine Urate Oxidase The above modified analogue protein of canine urate oxidase sample was dialysed overnight in 20 mM PB, pH 8.0, and ultrafiltrated (50 KD of Saturous angential flow modular). The sample was then purified with Sephacryl S300 molecular sieve column (GE Inc., USA), with balanced buffer of 20 mM PB, pH 8.0, flow rate of 7.0 ml/min Absorbance at both 254 nm and 280 nm was detected. The first peak is the target protein, and the purity of the obtained PEGylated analogue protein of canine urate oxidase is over 98.0% by RP-HPLC and SEC-HPLC (FIG. 3).

EXAMPLE 3

Immunogenicity In Vivo of Purified Proteins with Different Modification Ratios

Modified analogue proteins of canine urate oxidase with modification ratios of 1:40, 1:80, 1:120, and 1:160 were purified as in Example 2 and subject to rat injection to detect IgG antibody titers. 24 rats of Kunming species (purchased from the Third Military Medical Univ.) were divided randomly into 4 groups (n=6), each injected with the above analogue protein of canine urate oxidase with different modification ratios at a dose of 1.0 mg/kg. The injection was performed once every 5 days with 6 times of continuous injections. At 96 hours after injection, 0.5 ml of blood was taken from ophthalmic vein capillaries, followed by 3000 rpm centrifugation for 15 min to separate serums. IgG antibody titers against non-modified analogue protein of canine urate oxidase were detected by routine ELISA method. Results show that, the IgG antibody titer against 1:40 modified analogue protein of canine urate oxidase is 1:500, the IgG antibody titer against 1:80 modified analogue protein of canine urate oxidase is 1:300, the IgG antibody titer against 1:120 modified analogue protein of canine urate oxidase is 1:120, and the IgG antibody titer against 1:160 modified analogue protein of canine urate oxidase is 1:80. Among 1:120 ~1:160 modification ratios, the difference in antibody titers is reduced. In consideration of the average degree of modification, 1:120~1:160 is determined as the optimal modification ratio.

EXAMPLE 4

Physico-Chemical Property of PEGylated Analogue Protein of Canine Urate Oxidase

1. Detection of the Average Degree of Modification

Samples of lyophilized and de-salted analogue protein of canine urate oxidase and PEGylated analogue protein of canine urate oxidase were diluted with ultrapure water to 0.2 mg/ml, 0.4 mg/ml, 0.6 mg/ml, 0.8 mg/ml, and 1 mg/ml, respectively. 0.5 ml of the above protein sample as well as 0.5 ml of ultrapure water as control was added with 0.5 ml of 4% sodium hydrogen carbonate, mixed, added with 0.5 ml of 0.1% TNBS, and then mixed again. Samples were incubated at 40 water bath for 2 hours, then added with 0.5 ml of 10% SDS and 0.25 ml of 1N HCl, and mixed. Ultrapure water was used as control to set zero at 335 nm in a ultraviolet spectrophotometer (TU-1810PC, purchased from PuXi Universal Apparatus Corp. Ltd., Beijing), and ultraviolet absorbance of samples were detected at 335 nm. Linear regression was performed with concentration as the X-axis and absorbance as the Y-axis to determine the slop k. The modification degree of PEGylated analogue protein of canine urate oxidase (%)= $(1-k_1/k_0) \times 100\%$, wherein: $k_1$ refers to the slope of PEGylated analogue protein of canine urate oxidase, and $k_0$ refers to the slope of analogue protein of canine urate oxidase.

Results show that each protein with 1:80 modification conjugates in average with 5.7 of 5 kDa mPEG; each protein with 1:120 modification conjugates in average with 7.9 of 5 kDa mPEG; and each protein with 1:160 modification conjugates in average with 9.6 of 5 kDa mPEG.

2. Detection of Modification Specificity

Samples of lyophilized and de-salted PEGylated analogue protein of canine urate oxidase with 1:160 modification was sequenced with the N-terminal 30 amino acids, which is MYKNDEVEFVRTGYGKDMVKVLHIQRDGKY (residues 1-30 of SEQ ID NO:5) prior to the modification and MYxNDEVEFVRTGYGKDMVKVLHIQRDGxY (SEQ ID NO:7) thereafter, wherein no charcteristic adsorption peak showed at the site of x. The amino acid corresponding to that site is Lys, indicating that the ε-amino of Lys residue is modified, whereas the N-terminal Met residue may be clearly detected, suggesting no modification thereon, and the modification method of the invention being specific to the ε-amino of Lys residue (FIG. 4).

Figure 5:
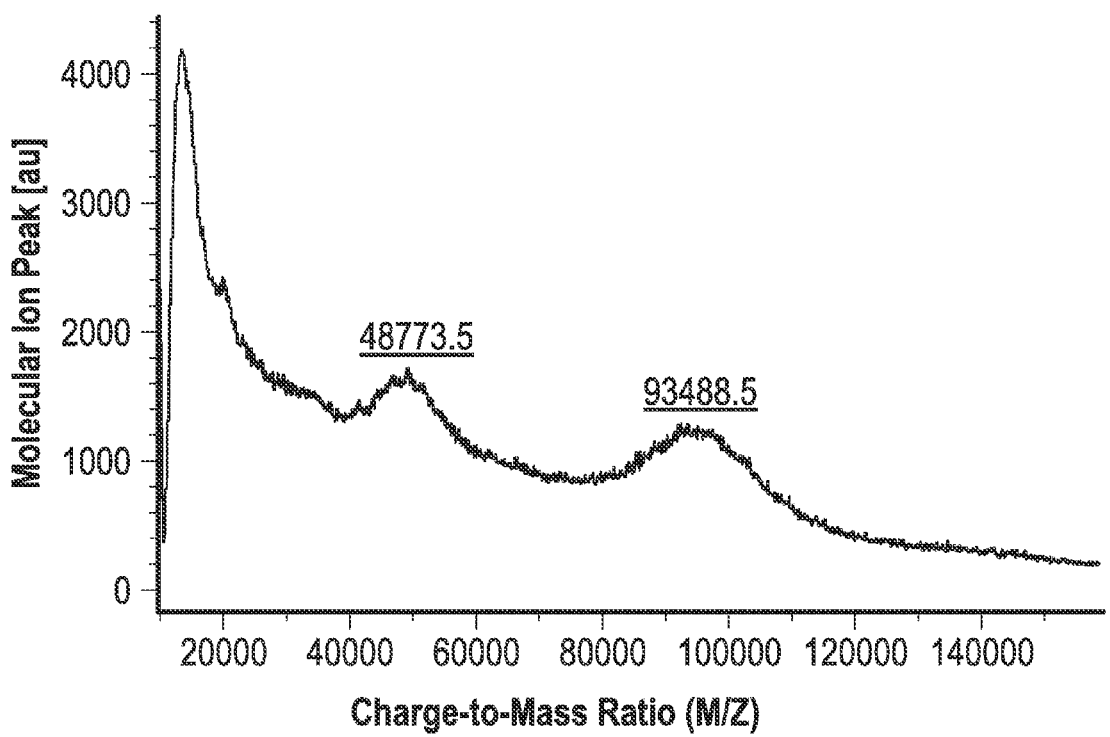
FIG. 5: Maldi-tof assay on PEGylated analogue protein of canine urate oxidase.

3. Molecular Weight Detection of PEGylated Analogue Protein of Canine Urate Oxidase Samples of lyophilized and de-salted PEGylated analogue protein of canine urate oxidase with 1:160 modification was subject to Maldi-tof (Bruker AutoflexII) for the detection of molecular weight. As is shown in FIG. 5, the molecular weight of modified protein is 93488.5, which is a little bit higher than that calculated from the average modification degree.

EXAMPLE 5

Figure 6:
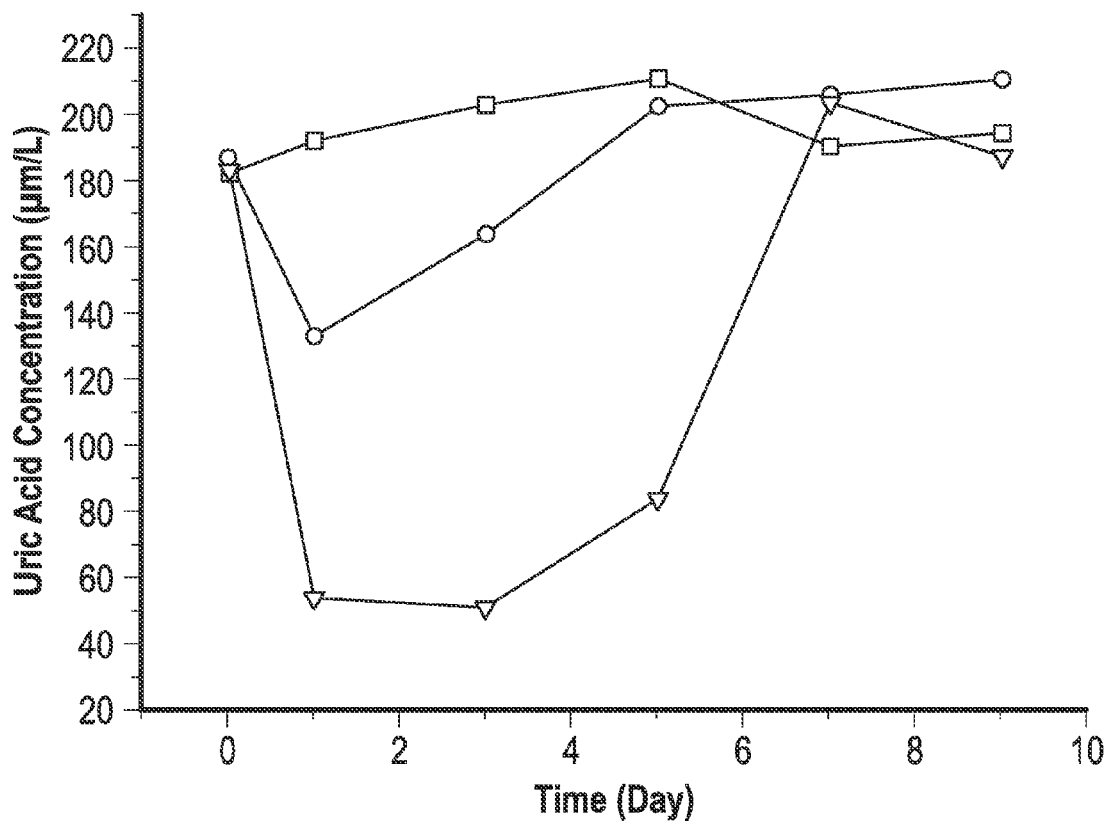
FIG. 6: The effect of PEGylated analogue protein of canine urate oxidase on the decrease of normal chicken blood uric acid, wherein ■ represents control group, ● represents non-modified analogue protein of canine urate oxidase group, and ▼ represents PEGylated analogue protein of canine urate oxidase group.

Pharmacodynamics Study on PEGylated Analogue Protein of Canine Urate Oxidase In Vivo 1. Effect of PEGylated Analogue Protein of Canine Urate Oxidase Decrease on Normal Chicken Blood Uric Acid 30 normal chickens (purchased from Deyang, Chengdu, China) were ordered by gender and the blood uric acid level prior to administration, and divided randomly into 3 groups, namely, non-modified analogue protein of canine urate oxidase group, PEGylated analogue protein of canine urate oxidase group, and control group, 10 for each group with half male and half female. With or without modification, the dose of the analogue protein of canine urate oxidase was both 1.0 mg/kg. Chickens were fed with water and no food for 16 hours before the administration and 1, 3, 5, 6, 7 and 9 days after a single administration. Blood was sampled from the wing vein, then subject to 3000 rpm/min of centrifugation to separate plasma. Serum uric acid was determined using HPLC method. Results show that (see FIG. 6) the blood uric acid concentration in normal chicken control group is constant at 220 μM; and with the injection of 5 kDa PEGylated analogue protein of canine urate oxidase, the blood uric acid concentration may be stabilized below 50 μM in 3~5 days, whereas the injection of non-modified analogue protein of canine urate oxidase decreases the blood uric acid concentration to merely about 130 μM in 1 day, then gradually back to normal. The 5 kDa PEGylated analogue protein of canine urate oxidase exhibits favourable effects on the decrease of blood uric acid concentration.

2. Effect of PEGylated Analogue Protein of Canine Urate Oxidase on the Prevention of Rat Primary Uric Acid Nephropathy According to body weight, 30 male SD rats (purchased from the Third Military Medical Univ.) were divided randomly into 3 groups, namely, the blank control group, the model control group, and the PEGylated analogue protein of canine urate oxidase (1.0 mg/kg) group, 6 for each group. Except for the blank group, each group was daily intraperitoneally injected once with sodium urate at a dose of 100 mg/10 ml/kg, and fed with yeast powder in mixed diets; whereas the blank group was fed with normal feed. From Day 1, each group was administrated intravenously with drugs to be tested once in a week for a continuous 5 weeks. 0.5 ml of blood was taken from the ophthalmic vein of each animal group at 24 h before and after the $5^{th}$ administration, followed by 3000 rpm centrifugation for 15 min to separate serum, and then subject to HPLC detection of serum uric acid. With the blood obtained from 24 h after the $5^{th}$ administration, serum urea nitrogen and creatinine concentration were detected on a TMS-1024i fully automatic biochemical analyser from Japan. Rats were sacrificed by exsanguination after the last blood sampling, and kidney tissue at one side was taken for the histopathologic examination. Results show that, the uric acid concentration in vivo in the treatment group may be stabilized below 80 μM with creatinine significantly decreased ($p<0.05$), indicating protection effect for kidney injuries from hyperuricemia. Histopathology results show that, as compared to model control group, overall rating of the PEGylated analogue protein of canine urate oxidase group are all significantly decreased ($p<0.001$), indicating significantly alleviated kidney injuries after drug administration. Therefore, the PEGylated analogue protein of canine urate oxidase exhibits good protection effect towards high kidney injuries from uric acid in rats (see Table 2).

Figure 7:
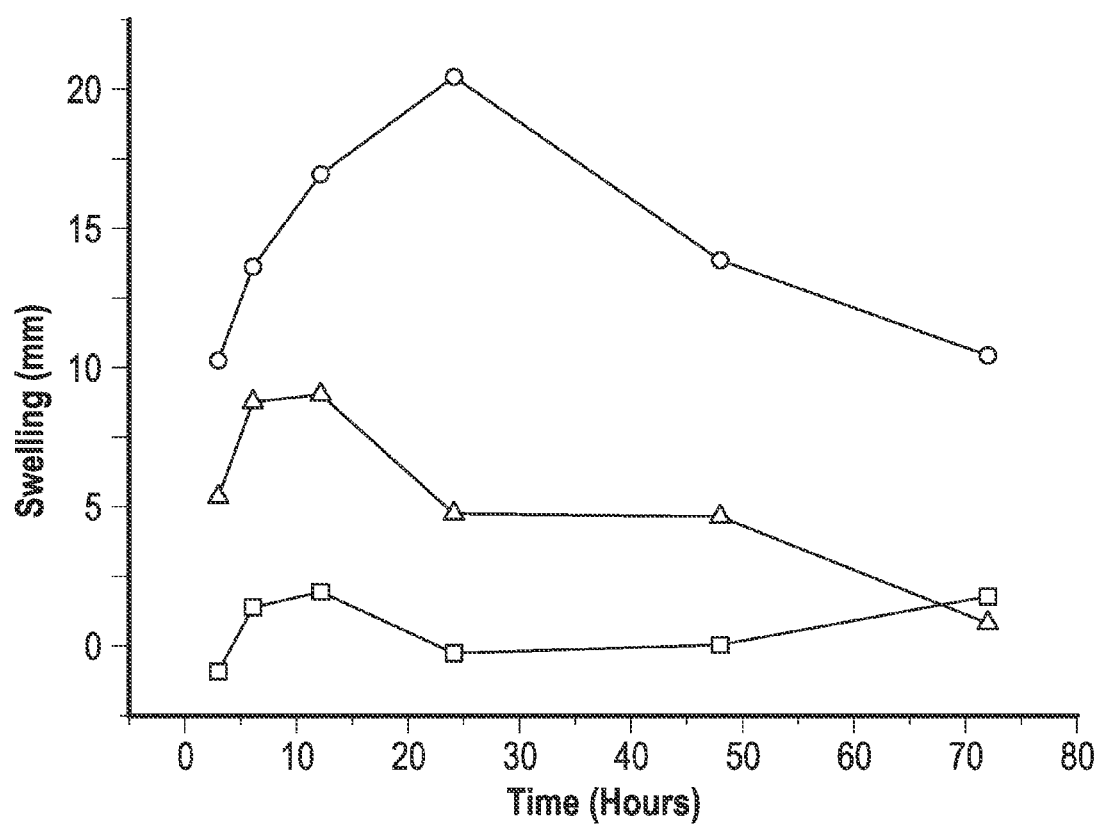
FIG. 7: The effect of PEGylated analogue protein of canine urate oxidase on the treatment of rabbit acute gouty arthritis, wherein ■ represents blank control group, ● represents model control group, and ▲ represents PEGylated analogue protein of canine urate oxidase group.

3. Effect of PEGylated Analogue Protein of Canine Urate Oxidase on the Treatment of Rabbit Acute Gouty Arthritis 18 male rabbits (purchased from the animal experiment center, the Third Military Medical Univ.) were divided randomly into blank group, model group, and PEGylated analogue protein of canine urate oxidase group (1.0 mg/kg), 6 for each group. Urate crystal (MSU) (from Sigma) was used to induce rabbit acute arthritis model, and except for the blank group, rabbits in each group were unhaired and sterilized at knee joints within 5 minutes after administration. To each rabbit, 0.3 ml of sterile MSU (100 mg/ml) suspension was injected into the intracavity of knee joint to induce inflammations, and meanwhile drugs to be tested were also administrated. Perimeter of the side joint with inflammation was detected with a tape at 3, 6, 12, 24, 48, and 72 h before and after the inflammation to calculate the degree of swelling (=Perimeter before minus Perimeter after the administration). Results show that (see FIG. 7), after the injection of sodium urate crystal, the model animal exhibits significant joint swelling with a maximum at 6 h, which is recovered to the extent as in blank control group at 24 h after the administration, indicating that injection of the 5 kDa PEGylated analogue protein of canine urate oxidase may significantly decrease joint swelling from sodium urate crystal.

EXAMPLE 6

Figure 8:
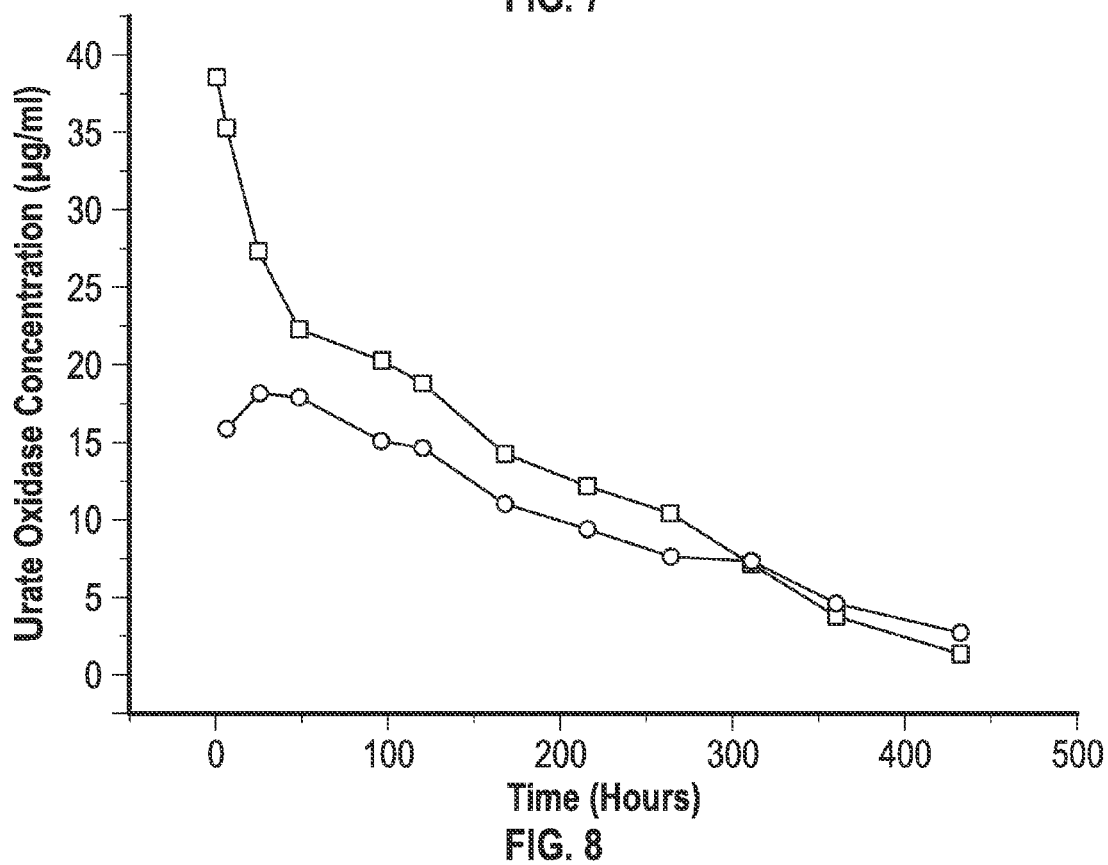
FIG. 8: Pharmacokinetics of PEGylated canine analogue protein of canine urate oxidase in cynomolgus monkey, wherein ■ represents intravenous administration and ● represents subcutaneous administration.

Detection of Pharmacokinetics and Subcutaneous Injection Bioavailability of PEGylated Analogue Protein of Canine Urate Oxidase The designed dose for clinical administration of the invention is 12 mg/person, i.e., 0.17 mg/kg (one person for 70 kg of body weight). The equivalent dose for rats is calculated according to body surface area formula of $dB=dA \times kB/kA=0.17$ mg/kg$\times 0.71/0.11 \approx 1.0$ mg/kg, with which pharmacokinetics and subcutaneous injection bioavailability for cynomolgus monkey was determined. Each group included 4 cynomolgus monkeys (purchased from the drug safety assessment center, Suzhou, China) with half male and half female. 1.5 ml of blood was taken from the upper limb elbow vein immediately (0 h), 10 min, 1 h, 6 h, 1 d, 2 d, 3 d, 6 d, 8 d, 10 d, 12 d, 15 d, 18 d and 21 d after the subcutaneous and intravenous administration, and placed in a heparinized tube, and then subject to 3000 rpm of centrifugation for 10 min to separate blood plasma and store at −80° C. to be tested. The blood uric acid concentration was calculated as the urate oxidase activity detection method in Example 1 (FIG. 8). Data points were fitted with two compartment model by drug metabolism calculation procedure DAS 2.0. The elimination half-time after a single subcutaneous and intravenous administration was respectively 187.8 hours and 137.6 hours, indicating that the injection thereof into a human body may also result in an elimination half-time of more than 1 week, thus

TABLE 2

| Groups | Before the $5^{th}$ administration (μM) | After the $5^{th}$ administration (μM) | Creatinine (μmol/L) | Urea nitrogen (μmol/L) |
|---|---|---|---|---|
| Blank control group | 40.70 ± 7.18 | 43.21 ± 13.69 | 69.56 ± 14.76 | 8.49 ± 1.75 |
| Model control group | 154.79 ± 40.25 | 124.1 ± 74.10 | 99.77 ± 18.47 | 8.98 ± 1.99 |
| PEGylated analogue protein of canine urate oxidase group | 76.03 ± 26.96 | 14.82 ± 14.32 | 81.67 ± 0.74 | 9.56 ± 4.36 | facilitating injection in every 1~2 weeks as desired. AUC (area under the curve) of the subcutaneous administration was calculated by statistical moment method, and, as compared to the AUC of equivalent intravenous administration, subcutaneous administration exhibited a bioavailability of 76.3%, suggesting the subcutaneous injection a route to be selected in human beings, which will improve the obedience for long-term treatment.

The invention claimed is:

1. A method for preparing a PEGylated analogue protein of canine urate oxidase, comprising:
   a. preparing a urate oxidase protein comprising more than 95.0% of tetramer analogue protein of canine urate oxidase prior to the PEGylation, wherein said analogue protein of canine urate oxidase is a chimeric protein which comprises amino acids of a canine urate oxidase and amino acids of a human urate oxidase, wherein the first 240 amino acids at the N-terminal of said chimeric protein are amino acids 1-240 of the canine urate oxidase and the following 64 amino acids are amino acids 241-304 of the human urate oxidase;
   b. PEGylating said analogue protein of canine urate oxidase, wherein the average molecular weight of said PEG is 1 kD~40 kD, and each monomer of said analogue protein of canine urate oxidase is conjugated in average with 2~15 PEG molecules;
   c. separating and purifying said PEGylated analogue protein.

2. The method of claim 1, wherein,
   in said step a, the preparation of analogue protein of canine urate oxidase prior to the PEGylation comprises using molecular sieve chromatography or ion exchange chromatography; and/or
   in said step b, said PEGylating the analogue protein of canine urate oxidase comprises using a molar ratio of said protein to the PEGylating agent of 1:40~1:200, and using a carbonate buffer solution in the conjugation system, wherein the pH of the carbonate buffer solution ranges from 8.0~11.0, and the ion strength of the carbonate buffer solution ranges from 10~200 mmol/L; and/or
   in said step c, chromatography and/or ultrafiltration are employed for the separation and purification of said PEGylated analogue protein of canine urate oxidase, wherein said methods for the separation and purification include molecular sieve chromatography, ion exchage chromatography, hydrophobic chromatography, or tangential flow ultrafiltration.

3. The method according to claim 2, wherein ion exchange chromatography is used for the preparation of said analogue protein of canine urate oxidase.

4. The method according to claim 2, wherein the molar ratio of said analogue protein of canine urate oxidase to the PEGylating agent is 1:120~1:160.

5. The method according to claim 2, wherein the pH ranges from 9.5~10.5 and the ion strength ranges from 50~150 mmol/L in said carbonate buffer.

6. The method according to claim 1, wherein said chimeric protein has an amino acid sequence selected from the group consisting of SEQ ID NO: 2, SEQ ID NO: 3, and SEQ ID NO: 4.

7. The method according to claim 1, wherein PEGylation sites of said analogue protein of canine urate oxidase include the N-terminal α-amino group and/or the ε-amino group at the Lys residue of the analogue protein of canine urate oxidase.

8. The method according to claim 1, wherein said analogue protein of canine urate oxidase is linked to an active group of PEG via an amino ester, secondary amine or amide linkage.

9. The method according to claim 1, wherein prior to the PEGylation of said analogue protein of canine urate oxidase, PEG needs to be activated, wherein active groups linked to one end of PEG for the activation include succinimidyl, nitrophenyl, amido, imido, carbamate, aldehydyl or histidinyl group; and blocking groups linked to the other end of PEG during the activation include monomethoxy, ethoxy, propoxy, butoxy, galactose or dextrose.

10. The method according to claim 9, wherein the active group linked to one end of PEG for the activation is a succinimidyl propionate (SPA) group or nitrophenyl carbonate (NPC) group.

11. The method according to claim 9, wherein said PEG is branch-chained or linear-chained; and the average molecular weight of said PEG is 5 kDa~20 kDa; and each monomer of said analogue protein of canine urate oxidase is conjugated in average with 4~12 PEG molecules.

12. The method according to claim 11, wherein the average molecular weight of said PEG is 5 kDa.

13. The method according to claim 11, wherein each monomer of said analogue protein of canine urate oxidase is conjugated in average with 6~11 PEG molecules.

* * * * *

```
                        SEQUENCE LISTING

<160> NUMBER OF SEQ ID NOS: 7

<210> SEQ ID NO 1
<211> LENGTH: 304
<212> TYPE: PRT
<213> ORGANISM: Canis familiaris

<400> SEQUENCE: 1

Met Ala His Tyr His Asn Asp Tyr Lys Lys Asn Asp Glu Val Glu Phe
1               5                   10                  15

Val Arg Thr Gly Tyr Gly Lys Asp Met Val Lys Val Leu His Ile Gln
            20                  25                  30

Arg Asp Gly Lys Tyr His Ser Ile Lys Glu Val Ala Thr Ser Val Gln
        35                  40                  45

Leu Thr Leu Ser Ser Lys Lys Asp Tyr Val Tyr Gly Asp Asn Ser Asp
    50                  55                  60

Ile Ile Pro Thr Asp Thr Ile Lys Asn Thr Val His Val Leu Ala Lys
65                  70                  75                  80

Phe Lys Gly Ile Lys Ser Ile Glu Thr Phe Ala Met Asn Ile Cys Glu
                85                  90                  95

His Phe Leu Ser Ser Phe Asn His Val Ile Arg Ala Gln Val Tyr Val
            100                 105                 110

Glu Glu Val Pro Trp Lys Arg Phe Glu Lys Asn Gly Val Lys His Val
        115                 120                 125

His Ala Phe Ile His Asn Pro Thr Gly Thr His Phe Cys Glu Val Glu
    130                 135                 140

Gln Met Arg Ser Gly Pro Pro Val Ile His Ser Gly Ile Lys Asp Leu
145                 150                 155                 160

Lys Val Leu Lys Thr Thr Gln Ser Gly Phe Glu Gly Phe Ile Lys Asp
                165                 170                 175

Gln Phe Thr Thr Leu Pro Glu Val Lys Asp Arg Cys Phe Ala Thr Lys
            180                 185                 190

Val Tyr Cys Lys Trp Arg Tyr His Gln Gly Arg Asp Val Asp Phe Glu
        195                 200                 205

Ala Thr Trp Asp Thr Val Arg Asp Ile Val Leu Glu Lys Phe Ala Gly
    210                 215                 220

Pro Tyr Asp Lys Gly Glu Tyr Ser Pro Ser Val Gln Lys Thr Leu Tyr
225                 230                 235                 240

Asp Ile Gln Val His Ser Leu Ser Arg Val Pro Glu Met Glu Asp Met
                245                 250                 255

Glu Ile Ser Leu Pro Asn Ile His Tyr Phe Asn Ile Asp Met Ser Lys
            260                 265                 270

Met Gly Leu Ile Asn Lys Glu Glu Val Leu Leu Pro Leu Asp Asn Pro
        275                 280                 285

Tyr Gly Arg Ile Thr Gly Thr Ala Lys Arg Lys Leu Ala Ser Lys Leu
    290                 295                 300

<210> SEQ ID NO 2
<211> LENGTH: 304
<212> TYPE: PRT
<213> ORGANISM: Artificial Sequence
<220> FEATURE:
```

<223> OTHER INFORMATION: synthetic construct

<400> SEQUENCE: 2

Met Ala His Tyr His Asn Asp Tyr Lys Lys Asn Asp Glu Val Glu Phe
1               5                   10                  15

Val Arg Thr Gly Tyr Gly Lys Asp Met Val Lys Val Leu His Ile Gln
            20                  25                  30

Arg Asp Gly Lys Tyr His Ser Ile Lys Glu Val Ala Thr Ser Val Gln
        35                  40                  45

Leu Thr Leu Ser Ser Lys Lys Asp Tyr Val Tyr Gly Asp Asn Ser Asp
50                  55                  60

Ile Ile Pro Thr Asp Thr Ile Lys Asn Thr Val His Val Leu Ala Lys
65                  70                  75                  80

Phe Lys Gly Ile Lys Ser Ile Glu Thr Phe Ala Met Asn Ile Cys Glu
                85                  90                  95

His Phe Leu Ser Ser Phe Asn His Val Ile Arg Ala Gln Val Tyr Val
            100                 105                 110

Glu Glu Val Pro Trp Lys Arg Phe Glu Lys Asn Gly Val Lys His Val
        115                 120                 125

His Ala Phe Ile His Asn Pro Thr Gly Thr His Phe Cys Glu Val Glu
130                 135                 140

Gln Met Arg Ser Gly Pro Pro Val Ile His Ser Gly Ile Lys Asp Leu
145                 150                 155                 160

Lys Val Leu Lys Thr Thr Gln Ser Gly Phe Glu Gly Phe Ile Lys Asp
                165                 170                 175

Gln Phe Thr Thr Leu Pro Glu Val Lys Asp Arg Cys Phe Ala Thr Lys
            180                 185                 190

Val Tyr Cys Lys Trp Arg Tyr His Gln Gly Arg Asp Val Asp Phe Glu
        195                 200                 205

Ala Thr Trp Asp Thr Val Arg Asp Ile Val Leu Glu Lys Phe Ala Gly
210                 215                 220

Pro Tyr Asp Lys Gly Glu Tyr Ser Pro Ser Val Gln Lys Thr Leu Tyr
225                 230                 235                 240

Asp Ile Gln Val Leu Ser Leu Ser Arg Val Pro Ala Ile Glu Asp Met
                245                 250                 255

Glu Ile Ser Leu Pro Asn Ile His Tyr Phe Asn Ile Asp Met Ser Lys
            260                 265                 270

Met Gly Leu Ile Asn Lys Glu Glu Val Leu Leu Pro Leu Asp Asn Pro
        275                 280                 285

Tyr Gly Lys Ile Thr Gly Thr Val Lys Arg Lys Leu Ser Ser Arg Leu
290                 295                 300

<210> SEQ ID NO 3
<211> LENGTH: 304
<212> TYPE: PRT
<213> ORGANISM: Artificial Sequence
<220> FEATURE:
<223> OTHER INFORMATION: synthetic construct

<400> SEQUENCE: 3

Met Ala His Tyr His Asn Asp Tyr Lys Lys Asn Asp Glu Val Glu Phe
1               5                   10                  15

Val Arg Thr Gly Tyr Gly Lys Asp Met Val Lys Val Leu His Ile Gln
            20                  25                  30

Arg Asp Gly Lys Tyr His Ser Ile Lys Glu Val Ala Thr Ser Val Gln
        35                  40                  45

Leu Thr Leu Ser Ser Lys Lys Asp Tyr Val Tyr Gly Asp Asn Ser Asp
            50                  55                  60

Ile Ile Pro Thr Asp Thr Ile Lys Asn Thr Val His Val Leu Ala Lys
 65                  70                  75                  80

Phe Lys Gly Ile Lys Ser Ile Glu Thr Phe Ala Met Asn Ile Cys Glu
                85                  90                  95

His Phe Leu Ser Ser Phe Asn His Val Ile Arg Ala Gln Val Tyr Val
            100                 105                 110

Glu Val Pro Trp Lys Arg Phe Glu Lys Asn Gly Val Lys His Val
            115                 120                 125

His Ala Phe Ile His Asn Pro Thr Gly Thr His Phe Cys Glu Val Glu
            130                 135                 140

Gln Met Arg Ser Gly Pro Pro Val Ile His Ser Gly Ile Lys Asp Leu
145                 150                 155                 160

Lys Val Leu Lys Thr Thr Gln Ser Gly Phe Glu Gly Phe Ile Lys Asp
                165                 170                 175

Gln Phe Thr Thr Leu Pro Glu Val Lys Asp Arg Cys Phe Ala Thr Lys
            180                 185                 190

Val Tyr Cys Lys Trp Arg Tyr His Gln Gly Arg Asp Val Asp Phe Glu
            195                 200                 205

Ala Thr Trp Asp Thr Val Arg Asp Ile Val Leu Glu Lys Phe Ala Gly
210                 215                 220

Pro Tyr Asp Lys Gly Glu Tyr Ser Pro Ser Val Gln Lys Thr Leu Tyr
225                 230                 235                 240

Asp Ile Gln Val Leu Thr Leu Gly Gln Val Pro Ala Ile Glu Asp Met
                245                 250                 255

Glu Ile Ser Leu Pro Asn Ile His Tyr Phe Asn Ile Asp Met Ser Lys
            260                 265                 270

Met Gly Leu Ile Asn Lys Glu Glu Val Leu Leu Pro Leu Asp Asn Pro
            275                 280                 285

Tyr Gly Lys Ile Thr Gly Thr Val Lys Arg Lys Leu Ser Ser Arg Leu
            290                 295                 300

<210> SEQ ID NO 4
<211> LENGTH: 304
<212> TYPE: PRT
<213> ORGANISM: Artificial Sequence
<220> FEATURE:
<223> OTHER INFORMATION: synthetic construct

<400> SEQUENCE: 4

Met Ala His Tyr His Asn Asp Tyr Lys Lys Asn Asp Glu Val Glu Phe
 1               5                  10                  15

Val Arg Thr Gly Tyr Gly Lys Asp Met Val Lys Val Leu His Ile Gln
                20                  25                  30

Arg Asp Gly Lys Tyr His Ser Ile Lys Glu Val Ala Thr Ser Val Gln
            35                  40                  45

Leu Thr Leu Ser Ser Lys Lys Asp Tyr Val Tyr Gly Asp Asn Ser Asp
            50                  55                  60

Ile Ile Pro Thr Asp Thr Ile Lys Asn Thr Val His Val Leu Ala Lys
 65                  70                  75                  80

Phe Lys Gly Ile Lys Ser Ile Glu Thr Phe Ala Met Asn Ile Cys Glu
                85                  90                  95

His Phe Leu Ser Ser Phe Asn His Val Ile Arg Ala Gln Val Tyr Val
            100                 105                 110

```
Glu Glu Val Pro Trp Lys Arg Phe Glu Lys Asn Gly Val Lys His Val
            115                 120                 125

His Ala Phe Ile His Asn Pro Thr Gly Thr His Phe Cys Glu Val Glu
        130                 135                 140

Gln Met Arg Ser Gly Pro Pro Val Ile His Ser Gly Ile Lys Asp Leu
145                 150                 155                 160

Lys Val Leu Lys Thr Thr Gln Ser Gly Phe Glu Gly Phe Ile Lys Asp
                165                 170                 175

Gln Phe Thr Thr Leu Pro Glu Val Lys Asp Arg Cys Phe Ala Thr Lys
            180                 185                 190

Val Tyr Cys Lys Trp Arg Tyr His Gln Gly Arg Asp Val Asp Phe Glu
        195                 200                 205

Ala Thr Trp Asp Thr Val Arg Asp Ile Val Leu Glu Lys Phe Ala Gly
    210                 215                 220

Pro Tyr Asp Lys Gly Glu Tyr Ser Pro Ser Val Gln Lys Thr Leu Tyr
225                 230                 235                 240

Asp Ile Gln Val His Ser Leu Ser Arg Val Pro Glu Met Glu Asp Met
                245                 250                 255

Glu Ile Ser Leu Pro Asn Ile His Tyr Phe Asn Ile Asp Met Ser Lys
            260                 265                 270

Met Gly Leu Ile Asn Lys Glu Glu Val Leu Leu Pro Leu Asp Asn Pro
        275                 280                 285

Tyr Gly Lys Ile Thr Gly Thr Val Lys Arg Lys Leu Ser Ser Arg Leu
    290                 295                 300

<210> SEQ ID NO 5
<211> LENGTH: 297
<212> TYPE: PRT
<213> ORGANISM: Artificial Sequence
<220> FEATURE:
<223> OTHER INFORMATION: synthetic construct

<400> SEQUENCE: 5

Met Tyr Lys Asn Asp Glu Val Glu Phe Val Arg Thr Gly Tyr Gly Lys
1               5                   10                  15

Asp Met Val Lys Val Leu His Ile Gln Arg Asp Gly Lys Tyr His Ser
            20                  25                  30

Ile Lys Glu Val Ala Thr Ser Val Gln Leu Thr Leu Ser Ser Lys Lys
        35                  40                  45

Asp Tyr Val Tyr Gly Asp Asn Ser Asp Ile Ile Pro Thr Asp Thr Ile
    50                  55                  60

Lys Asn Thr Val His Val Leu Ala Lys Phe Lys Gly Ile Lys Ser Ile
65                  70                  75                  80

Glu Thr Phe Ala Met Asn Ile Cys Glu His Phe Leu Ser Ser Phe Asn
                85                  90                  95

His Val Ile Arg Ala Gln Val Tyr Val Glu Glu Val Pro Trp Lys Arg
            100                 105                 110

Phe Glu Lys Asn Gly Val Lys His Val His Ala Phe Ile His Asn Pro
        115                 120                 125

Thr Gly Thr His Phe Cys Glu Val Glu Gln Met Arg Ser Gly Pro Pro
    130                 135                 140

Val Ile His Ser Gly Ile Lys Asp Leu Lys Val Leu Lys Thr Thr Gln
145                 150                 155                 160

Ser Gly Phe Glu Gly Phe Ile Lys Asp Gln Phe Thr Thr Leu Pro Glu
                165                 170                 175
```

```
Val Lys Asp Arg Cys Phe Ala Thr Lys Val Tyr Cys Lys Trp Arg Tyr
            180                 185                 190

His Gln Gly Arg Asp Val Asp Phe Glu Ala Thr Trp Asp Thr Val Arg
            195                 200                 205

Asp Ile Val Leu Glu Lys Phe Ala Gly Pro Tyr Asp Lys Gly Glu Tyr
    210                 215                 220

Ser Pro Ser Val Gln Lys Thr Leu Tyr Asp Ile Gln Val His Ser Leu
225                 230                 235                 240

Ser Arg Val Pro Glu Met Glu Asp Met Glu Ile Ser Leu Pro Asn Ile
                245                 250                 255

His Tyr Phe Asn Ile Asp Met Ser Lys Met Gly Leu Ile Asn Lys Glu
            260                 265                 270

Glu Val Leu Leu Pro Leu Asp Asn Pro Tyr Gly Lys Ile Thr Gly Thr
            275                 280                 285

Val Lys Arg Lys Leu Ser Ser Arg Leu
    290                 295

<210> SEQ ID NO 6
<211> LENGTH: 301
<212> TYPE: PRT
<213> ORGANISM: Artificial Sequence
<220> FEATURE:
<223> OTHER INFORMATION: synthetic construct

<400> SEQUENCE: 6

Met Ala His Tyr His Asn Asp Tyr Lys Lys Asn Asp Glu Val Glu Phe
1               5                   10                  15

Val Arg Thr Gly Tyr Gly Lys Asp Met Val Lys Val Leu His Ile Gln
            20                  25                  30

Arg Asp Gly Lys Tyr His Ser Ile Lys Glu Val Ala Thr Ser Val Gln
        35                  40                  45

Leu Thr Leu Ser Ser Lys Lys Asp Tyr Val Tyr Gly Asp Asn Ser Asp
    50                  55                  60

Ile Ile Pro Thr Asp Thr Ile Lys Asn Thr Val His Val Leu Ala Lys
65                  70                  75                  80

Phe Lys Gly Ile Lys Ser Ile Glu Thr Phe Ala Met Asn Ile Cys Glu
                85                  90                  95

His Phe Leu Ser Ser Phe Asn His Val Ile Arg Ala Gln Val Tyr Val
            100                 105                 110

Glu Glu Val Pro Trp Lys Arg Phe Glu Lys Asn Gly Val Lys His Val
        115                 120                 125

His Ala Phe Ile His Asn Pro Thr Gly Thr His Phe Cys Glu Val Glu
    130                 135                 140

Gln Met Arg Ser Gly Pro Pro Val Ile His Ser Gly Ile Lys Asp Leu
145                 150                 155                 160

Lys Val Leu Lys Thr Thr Gln Ser Gly Phe Glu Gly Phe Ile Lys Asp
                165                 170                 175

Gln Phe Thr Thr Leu Pro Glu Val Lys Asp Arg Cys Phe Ala Thr Lys
            180                 185                 190

Val Tyr Cys Lys Trp Arg Tyr His Gln Gly Arg Asp Val Asp Phe Glu
        195                 200                 205

Ala Thr Trp Asp Thr Val Arg Asp Ile Val Leu Glu Lys Phe Ala Gly
    210                 215                 220

Pro Tyr Asp Lys Gly Glu Tyr Ser Pro Ser Val Gln Lys Thr Leu Tyr
225                 230                 235                 240
```

```
Asp Ile Gln Val His Ser Leu Ser Arg Val Pro Glu Met Glu Asp Met
                245                 250                 255

Glu Ile Ser Leu Pro Asn Ile His Tyr Phe Asn Ile Asp Met Ser Lys
            260                 265                 270

Met Gly Leu Ile Asn Lys Glu Glu Val Leu Leu Pro Leu Asp Asn Pro
        275                 280                 285

Tyr Gly Lys Ile Thr Gly Thr Val Lys Arg Lys Leu Ser
    290                 295                 300

<210> SEQ ID NO 7
<211> LENGTH: 30
<212> TYPE: PRT
<213> ORGANISM: Artificial Sequence
<220> FEATURE:
<223> OTHER INFORMATION: synthetic construct
<220> FEATURE:
<221> NAME/KEY: SITE
<222> LOCATION: 3, 29
<223> OTHER INFORMATION: Xaa = modified sigma-amino acid of Lysine

<400> SEQUENCE: 7

Met Tyr Xaa Asn Asp Glu Val Glu Phe Val Arg Thr Gly Tyr Gly Lys
1               5                   10                  15

Asp Met Val Lys Val Leu His Ile Gln Arg Asp Gly Xaa Tyr
            20                  25                  30
```